United States Patent
Mandadi et al.

(10) Patent No.: US 11,041,143 B2
(45) Date of Patent: *Jun. 22, 2021

(54) METHODS, COMPOSITIONS, AND SYSTEMS FOR CULTURING AND CHARACTERIZING FASTIDIOUS PLANT MICROBES

(71) Applicant: THE TEXAS A&M UNIVERSITY SYSTEM, College Station, TX (US)

(72) Inventors: Kranthi K. Mandadi, Weslaco, TX (US); Sonia C. Irigoyen, Weslaco, TX (US); T. Erik Mirkov, Harlingen, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 224 days.

This patent is subject to a terminal disclaimer.

(21) Appl. No.: 15/353,645

(22) Filed: Nov. 16, 2016

(65) Prior Publication Data

US 2017/0137776 A1 May 18, 2017

Related U.S. Application Data

(60) Provisional application No. 62/255,823, filed on Nov. 16, 2015.

(51) Int. Cl.
| | |
|---|---|
| *C12N 15/82* | (2006.01) |
| *C12N 1/20* | (2006.01) |
| *A01H 4/00* | (2006.01) |
| *C12N 5/04* | (2006.01) |
| *C12Q 1/02* | (2006.01) |
| *C12Q 1/689* | (2018.01) |

(52) U.S. Cl.
CPC .............. *C12N 1/20* (2013.01); *A01H 4/005* (2013.01); *C12N 5/04* (2013.01); *C12N 15/8241* (2013.01); *C12Q 1/025* (2013.01); *C12Q 1/689* (2013.01); *C12N 2502/70* (2013.01); *C12Q 2600/158* (2013.01); *G01N 2333/195* (2013.01); *G01N 2333/415* (2013.01)

(58) Field of Classification Search
None
See application file for complete search history.

(56) References Cited

U.S. PATENT DOCUMENTS

| | | | |
|---|---|---|---|
| 2008/0153102 A1 | 6/2008 | Huang et al. | |
| 2009/0126038 A1* | 5/2009 | Van De Craen | C12N 15/111 800/278 |

FOREIGN PATENT DOCUMENTS

CN 102766650 A 11/2012

OTHER PUBLICATIONS

Porter, Critical Reviews in Plant Sciences, 10(4):387-421 (1991). (Year: 1991).*
Li et al. (Journal of Microbiological Methods 78 (2009) 59-65). (Year: 2009).*
Estrada-Navarrete, et al. (Nature Protocols 2.7 (2007): 1819). (Year: 2007).*
Ferrari et al. (Applied And Environmental Microbiology, May 2009, p. 3352-3354). (Year: 2009).*
Kamagata et al. (Microbes and Environments 20.2 (2005): 85-91). (Year: 2005).*
Purcell et al. (Annu. Rev. Phytopathol. 1996. 34:131-51). (Year: 1996).*
Tada et al. (Science 321.5891 (2008): 952-956). (Year: 2008).*
Chen et al. "Establishing and Fine-Tuning an in Planta System for Potato Zebra Chip Disease Research in California" 2010 Zebra Chip Reporting Session (2010): 19. (Year: 2010).*
Sechler et al. (Phytopathology 99.5 (2009): 480-486). (Year: 2009).*
Mugnier, J. (Phytopathology 77.4 (1987): 539-542). (Year: 1987).*
Veena et al. (In Vitro Cell.Dev.Biol.—Plant (2007) 43:383-403). (Year: 2007).*
Mugnier, (Phytopathology 77.4 (1987): 539-542). (Year: 1987).*
Rennie et al. (Eur J Plant Pathol (2013) 135:771-781). (Year: 2013).*
Qu et al. (Journal of eukaryotic microbiology 54.6 (2007): 465-467). (Year: 2007).*
Collier et al. (The Plant Journal 43.3 (2005): 449-457). (Year: 2005).*
Taylor et al. (Agrobacterium Protocols. Humana Press, 2006. 155-168). (Year: 2006).*
International Search Report and Written Opinion dated Feb. 27, 2017 in connection with International Application No. PCT/US2016/062342, 9 pages.
Katherine Noorda-Nguyen, et al., "Agrobacterium rhizogenes Generates Transgenic Hairy Roots in Carica papaya L.: A New Approach for Studying and Improving Resistance to the Root-rot Pathogen, Phytophthora palmivora", Transgenic Plant Journal, 2010, vol. 4, No. 1, pp. 94-96.
David Gilchrist, et al., "Application of Agrobacterium Rhizogenes-Mediated Transformation Strategies for a Rapid High Throughput Screen for Genetic Resistance to Pierce's Disease in Grape that Maintains the Clonal Integrity of the Recipient Host", Pierce's Disease Research Symposium, Dec. 15-18, 2002, San Diego, California, pp. 11-12.

(Continued)

*Primary Examiner* — Charles Logsdon
(74) *Attorney, Agent, or Firm* — Hogan Lovells US LLP

(57) ABSTRACT

Numerous plant microbes, including the vascular-limited *Candidatus* spp.—causal agents of citrus greening and potato zebra chip diseases—are non-culturable. The present disclosure relates, according to some embodiments, to compositions, methods and systems for culturing such organisms. For example, the present disclosure relates to methods for culturing, propagating, and characterizing fastidious vascular-colonizing microbes using a hairy root system (e.g., in vitro, in planta). The present disclosure relates, in some embodiments, to methods for cultivating a fastidious plant microbe including: contacting a plant (e.g., a tomato plant, a potato plant, a citrus plant) colonized by a fastidious plant microbe (e.g., *Xylella fastidiosa*, *Candidatus Liberibacter* spp.) with a suspension of *R. rhizogenes* under conditions that permit induction of hairy roots colonized with the fastidious plant microbe, and propagating the colonized microbial hairy roots.

23 Claims, 21 Drawing Sheets

(56) References Cited

OTHER PUBLICATIONS

Attila Kereszt, et al., "Agrobacterium Rhizogenes-Mediated Transformation of Soybean to Study Root Biology", Nature Protocols, 2007, vol. 2, No. 4, pp. 948-952.
Mily Ron, et al., "Hairy Root Transformation Using Agrobacterium rhizogenes as a Tool for Exploring Cell Type-Specific Gene Expression and Function Using Tomato as a Model", Plant Physiology, Oct. 2014, vol. 166, pp. 455-469.
Sanghamitra Khandual, et al., "Rapid, Efficient and High-Performance Protocol for Agrobacterium rhizogenes-Mediated Hairy Root Transformation of the Common Bean *Phaseolus vulgaris*", Advances in Bioscience and Biotechnology, 2014, vol. 5, pp. 333-339.
B.C. Ferrari, et al., "Cultivation of Fastidious Bacteria by Viability Staining and Micromanipulation in a Soil Substrate Membrane System", Applied and Environmental Microbiology, May 2009, vol. 75, No. 10, pp. 3352-3354.
Qu Xinshun et al., "In vitro culture of the obligate parasite *Spongospora subterranean* (Cercozoa: Plasmodiiophorida) associated with root-inducing ransferred-DNA transformed potato hairy roots," Journal of Eukaryotic Microbiology, vol. 54, No. 6, Nov. 2007 pp. 465-467.
European Search Report dated May 15, 2019 issued in EP 16 867 069.3.
Fletcher et al., "Fastidious Vascular-Colonizing Bacteria," The Plant Health Instructor, DOI: 10.1094/PHI-I-2002-1218-02.
Merz, "Powdery Scab of Potato—Occurrence, Life Cyle and Epidemiology," Am. J. Pot. Res (2008) 85:241-246.
Thangavel et al., "Monitoring Spongospora subterranea Development in Potato Roots Reveals Distinct Infection Patterns and Enables Efficient Assessment of Disease Control Methods," PLOS ONE/DOI: 10.1371/journal.pone.0137647, Sep. 9, 2015.
Merfa et al., "Progress and Obstacles in Culturing Candidatus Liberibacter asicaticus, the Bacterium Associated with Huanglongbing," Phytopathology 2019, 109:1092-1101.
Bove et al., "Phloem- and xylem-restricted plant pathogenic bacteria," Plant Science 163 (2002) 1083-1098.
Kessmann et al., "Induction of Systemic Acquired Disease Resistance in Plants by Chemicals," Annu. Rev. Phytopathol. 1994, 32:439-59.
Heil et al., "Induces Systemic Resistance (ISR) Against Pathogens in the Context of induced Plant Defences," Annals of Botany 89:503-512, 2002.
Fletcher et al., "Fastidious Vascular-Colonizing Bacteria," https://www.apsnet.org/edcenter/disandpath/prokaryote/intro/Pages/Fastidious/aspx.
Ferrari et al., "Cultivation of Fastidious Bacteria by Viability Staining and Micromanipulation in a Soil Substrate Membrane System," Applied and Environmental Microbiology, May 2009, p. 3352-3354.
Desoignies Nicolas et al., In Vitro Dual Culture of Polymyxa betae in Agrobacterium rhyzogenes Transformed Sugar Beet Hairy Root in Liquid Media, Journal of Eukaryotic Microbiology (Sep. 2011), vol. 58, No. 5, pp. 424-425.
Mugnier J. "Establishment of New Axenic Hairy Root Lines by Inoculation with Agrobacterium-Rhyzogenes," Plant Cell Report, (1988), vol. 7, No. 1, ISSN 0721-7714, pp. 9-10.

* cited by examiner

METHODS, COMPOSITIONS, AND SYSTEMS FOR CULTURING AND CHARACTERIZING FASTIDIOUS PLANT MICROBES

CROSS-REFERENCE TO RELATED APPLICATIONS

This application claims the benefit of U.S. Provisional Application No. 62/255,823 filed Nov. 16, 2015, the entire contents of which are hereby incorporated in this disclosure by reference.

GOVERNMENT LICENSE RIGHTS

This invention was made in part with government support under contract 2015-67030-24294, awarded by the United States Department of Agriculture. The government has certain rights in the invention.

FIELD OF THE DISCLOSURE

The present disclosure relates, in some embodiments, to methods, compositions, and systems for culturing and characterizing fastidious plant microbes.

BACKGROUND OF THE DISCLOSURE

Estimates of food and agriculture organizations project that global food production has to increase 60% by 2050 to meet the demands of the rising world population. On top of the rising demand, annual agricultural crop losses caused by plant pathogens may run into upwards of 40%. Fastidious and obligate phytopathogens alone may be devastating to several food and commodity crops. For example, xylem-limited *Xylella fastidiosa* infects over 100 plant species including grapevine, citrus, coffee and almonds. Similarly, phloem-limited *Candidatus Liberibacter* spp. are emerging destructive pathogens causing yield losses (e.g., severe losses) in diverse plant families, including Solanaceae (potato, tomato, pepper and tobacco), Apiaceae (carrot and celery), Rosaceae (pear, apple and blackthorn), and Rutaceae (citrus spp.). Zebra chip disease in potato may be caused by *Candidatus Liberibacter* solanacearum (Lso), which also infects tomatoes, pepper and tobacco. Lso is transmitted by an insect vector, potato psyllid (*Bactericera cockerelli*). Since being designated as an emerging disease in 2004, zebra chip disease has been documented in several commercial potato growing regions of the United States, Mexico, Central America, and New Zealand. In Texas alone, zebra chip disease is estimated to affect 35% of cultivated potato acreage, causing annual crop losses of approximately $25 million USD. Similarly, citrus greening or Huanglongbing (HLB) disease caused by the *Candidatus* Liberibacter asiaticus (Las) may be the most devastating disease of citrus today, and threatens citrus production worldwide. HLB is transmitted by the insect vector, Asian *Citrus* psyllid (*Diaphorina citri*). In 2006-2011, in Florida alone, HLB caused losses upwards of $4.5 billion USD. These and other diseases caused by fastidious plant pathogens are a major threat to U.S. and global agriculture production. It is imperative to curtail these agricultural losses in order to overcome the impending global food security challenge.

SUMMARY

The inability to culture fastidious vascular-limited microbes is a major bottleneck in research relating to several destructive agricultural pathogens, such as Lso and Las. Accordingly, a need has arisen for improved (e.g., easy, rapid, and/or scalable) culturing and functional characterization of fastidious vascular-colonizing microbes.

The present disclosure relates, in some embodiments, to methods, compositions, and systems for culturing and characterizing fastidious microbes using hairy roots (e.g., *R. rhizogenes*-mediated hairy roots induced directly from infected plants or plant tissues). *R. rhizogenes*-mediated hairy roots induced directly from the infected plants or plant tissues may provide an easy, rapid and scalable platform to culture and characterize the fastidious vascular-colonizing microbes. For example, Lso and Las may be cultured in hairy roots induced directly from Lso- and Las-infected tomato, potato and citrus plants or plant tissues. Because hairy roots are organized and stable tissues, the microbe-colonized hairy root tissues may be clonally propagated for numerous applications (e.g., characterization of the fastidious microbes).

The present disclosure relates, in some embodiments, to methods for cultivating a fastidious plant microbe (e.g., a fastidious plant pathogen). For example, a method may comprise contacting a plant (e.g., a tomato plant, a potato plant, a citrus plant) colonized by a fastidious plant microbe (e.g., *Xylella fastidiosa*, *Candidatus Liberibacter* spp.) with a suspension of *R. rhizogenes* under conditions that permit induction of hairy roots colonized with the fastidious plant microbe. A fastidious plant microbe may then be cultivated by propagating the colonized microbial hairy roots. In some embodiments, a cultivated plant microbe may be *Candidatus Liberibacter* spp. (e.g., *Candidatus Liberibacter* solanacearum (Lso) and/or *Candidatus Liberibacter* asiaticus (Las)). According to some embodiments, *R. rhizogenes* may include both a Ri-DNA plasmid and a T-DNA plasmid and the T-DNA plasmid may encode a first exogenous transgene (e.g., a gene encoding an autofluorescent protein). According to some embodiments, a plant may include a first exogenous transgene.

In some embodiments, contacting a plant colonized by a fastidious microbe with a suspension of *R. rhizogenes* may include wounding one or more surfaces of a plant, forming a wound site, and exposing the wound site to a suspension of *R. rhizogenes*. Contacting a plant colonized by a fastidious plant microbe with a suspension of *R. rhizogenes*, in some embodiments, may include removing a photosynthetic portion of the plant to generate a wound site. In some embodiments, a method may include covering a wound site with a rock wool matrix and exposing the rock wool matrix to a suspension of *R. rhizogenes*. According to some embodiments, a method may include submerging a wound site in a suspension of *R. rhizogenes*, vacuum infiltrating at least a portion of the suspension of *R. rhizogenes* into the wound site, and covering the wounds site with a vermiculite matrix. A method may comprise, in some embodiments, contacting any desired portion of a plant colonized with the fastidious plant microbe with *R. rhizogenes* including, for example, a cotyledon, a hypocotyl, an immature shoot, an immature root, a mature shoot, or mature root.

Propagating a colonized hairy root, according to some embodiments, may include exposing an attached hairy root or a harvested hairy root to one or more selective consitions. In some embodiments, propagating may include transferring an attached hairy root or a harvested hairy root to at least one of: a vermiculite matrix, a hydroponic system, an in vitro system, and a bioreactor system. A method may comprise assessing the presence of the fastidious plant pathogen in the propagated microbial hairy roots, according to some embodiments.

The present disclosure relates, in some embodiments, to methods for assessing an effect of a test composition on a fastidious plant microbe. A method may comprise, for example, contacting a plant (e.g., a tomato plant, a potato plant, a citrus plant) infected with the fastidious plant microbe (e.g., *Xylella fastidiosa, Candidatus Liberibacter* spp.) with *R. rhizogenes* under conditions that permit induction of hairy roots colonized by the fastidious plant microbe, propagating the colonized microbial hairy roots, contacting the propagated colonized microbial hairy roots with the test composition, and/or assessing at least one metric of the presence and/or vitality of the fastidious plant microbe. In some embodiments, a cultivated plant microbe may be *Candidatus Liberibacter* spp. (e.g., *Candidatus Liberibacter* solanacearum (Lso) and/or *Candidatus Liberibacter* asiaticus (Las)).

A method may comprise, in some embodiments, contacting *Rhizobium rhizogenes* with any desired portion of a plant colonized with a fastidious plant microbe including, for example, a cotyledon, a hypocotyl, an immature shoot, an immature root, a mature shoot, or mature root. In some embodiments, a test composition may be applied to and/or injected into an infected microbial hairy root. A test composition, in some embodiments, may be conditionally or constitutively present in an infected plant (e.g., a propagated infected hairy root).

According to some embodiments, a colonized plant (e.g., a propagated colonized hairy root) may comprise an exogenous transgene (e.g., NPR1, GFP) and the test composition may be or may comprise a gene product of the transgene. In some embodiments, a colonized plant (e.g., a propagated colonized microbial hairy root) may include at least one of an exogenous transgene, a CRISPR/Cas. A TALEN, and an RNAi construct, and accordingly a test composition may be or may comprise a gene product of the transgene, a CRISPR/Cas, a TALEN, and an RNAi construct. In some embodiment, a test composition may include an NPR1 protein.

The present disclosure relates, in some embodiments, to methods for culturing fastidious plant microbes using hairy roots. A method may comprise, for example, selecting tissues from one or more parts of a plant as an explant source; cultivating the explant source in an in vitro medium comprising *Rhizobium rhizogenes* (*R. rhizogenes*); cutting the explant source into a plurality of pieces; inducing growth of hairy roots from at least some pieces of the explant source over a period of time; performing polymerase chain reaction (PCR) amplification of *R. rhizogenes* root locus B (rolB) and *R. rhizogenes* root locus C (rolC) marker genes to confirm the induction of the hairy roots; and/or performing PCR amplification of a 16S rDNA marker genes to determine presence of one or more fastidious microbes. In some embodiments, an infected plant may comprise a first exogenous transgene and a second exogenous transgene. A first exogenous transgene may encode, for example, an autofluorescent protein (e.g., green fluorescent protein, yellow fluorescent protein, red fluorescent protein, and the like). According to some embodiments, cultivating the explant source in a medium comprising *R. rhizogenes* may comprise cultivating the explant source in a medium free of antibiotics (e.g., free of at least cefatoxime, carbencillin and kanamycin).

BRIEF DESCRIPTION OF THE DRAWINGS

FIG. 1 illustrates a workflow for generating microbial hairy roots for downstream studies and applications, according to example embodiments of the disclosure;

FIG. 2A illustrates adult psyllids being propagated in contained traps using eggplants as host plants, according to an embodiment of the disclosure;

FIG. 2B illustrates adult psyllids carrying Lso being propagated in contained traps using eggplants as host plants, according to an embodiment of the disclosure;

FIG. 2C illustrates healthy tomato leaves at four weeks post-psyllid exposure, according to an embodiment of the disclosure;

FIG. 2D illustrates Lso-infected tomato leaves at four weeks post-psyllid exposure, according to an embodiment of the disclosure;

FIG. 2E illustrates healthy potato leaves at four weeks post-psyllid exposure, according to an embodiment of the disclosure;

FIG. 2F illustrates Lso-infected tomato leaves at four weeks post-psyllid exposure, according to an embodiment of the disclosure;

FIG. 2G illustrates polymerase chain reaction (PCR)-based confirmation of Lso in infected tomato and potato leaves;

FIGS. 3A-3E illustrate, according to specific example embodiments of the disclosure, a schematic of an in vitro microbial hairy root platform;

FIG. 3A shows cutting of surface-sterilized plant tissues into smaller pieces and gentle wounding using a fine forceps, according to an embodiment of the disclosure;

FIG. 3B shows immersing explants in a suspension of *R. rhizogenes,* according to an embodiment of the disclosure;

FIG. 3C shows explants following three-day co-cultivation of the plant tissues on nutrient media, according to an embodiment of the disclosure;

FIG. 3D shows an osmotic stress treatment of explants, according to an example embodiment of the disclosure;

FIG. 3E shows incubation of the explants in nutrient selection media following the treatment of FIG. 3D, according to an embodiment of the disclosure;

FIG. 4A illustrates in vitro induction of hairy roots on a tomato explant transformed with *Rhizobium rhizogenes* (strain ATCC 15834), according to an embodiment of the disclosure;

FIG. 4B shows PCR validation results of hairy roots on a tomato explant, according to an embodiment of the disclosure;

FIG. 5A illustrates in vitro induction of hairy roots on a potato explant transformed with *Rhizobium rhizogenes,* according to an embodiment of the disclosure;

FIG. 5B shows PCR validation results of hairy roots on a potato explant, according to an embodiment of the disclosure;

FIGS. 6A illustrates in vitro induction of hairy roots on citrus (Eureka lemon) explants transformed with *Rhizobium rhizogenes* (strain ATCC 15834), according to an embodiment of the disclosure;

FIG. 6B shows PCR validation results of hairy roots on citrus (Eureka lemon) explants transformed with *Rhizobium rhizogenes* (strain ATCC 15834), according to an embodiment of the disclosure;

FIG. 7A shows aerial hairy roots induced on a healthy tomato by *Rhizobium rhizogenes,* according to an embodiment of the disclosure;

FIG. 7B shows aerial microbial hairy roots induced on an Lso-colonized tomato by *Rhizobium rhizogenes,* according to an embodiment of the disclosure;

FIG. 7C shows PCR validation results of aerial hairy roots on tomato, according to an embodiment of the disclosure;

FIG. 8A shows aerial hairy roots induced on an Lso-colonized potato by *Rhizobium rhizogenes*, according to an embodiment of the disclosure;

DETAILED DESCRIPTION

Figure 1:
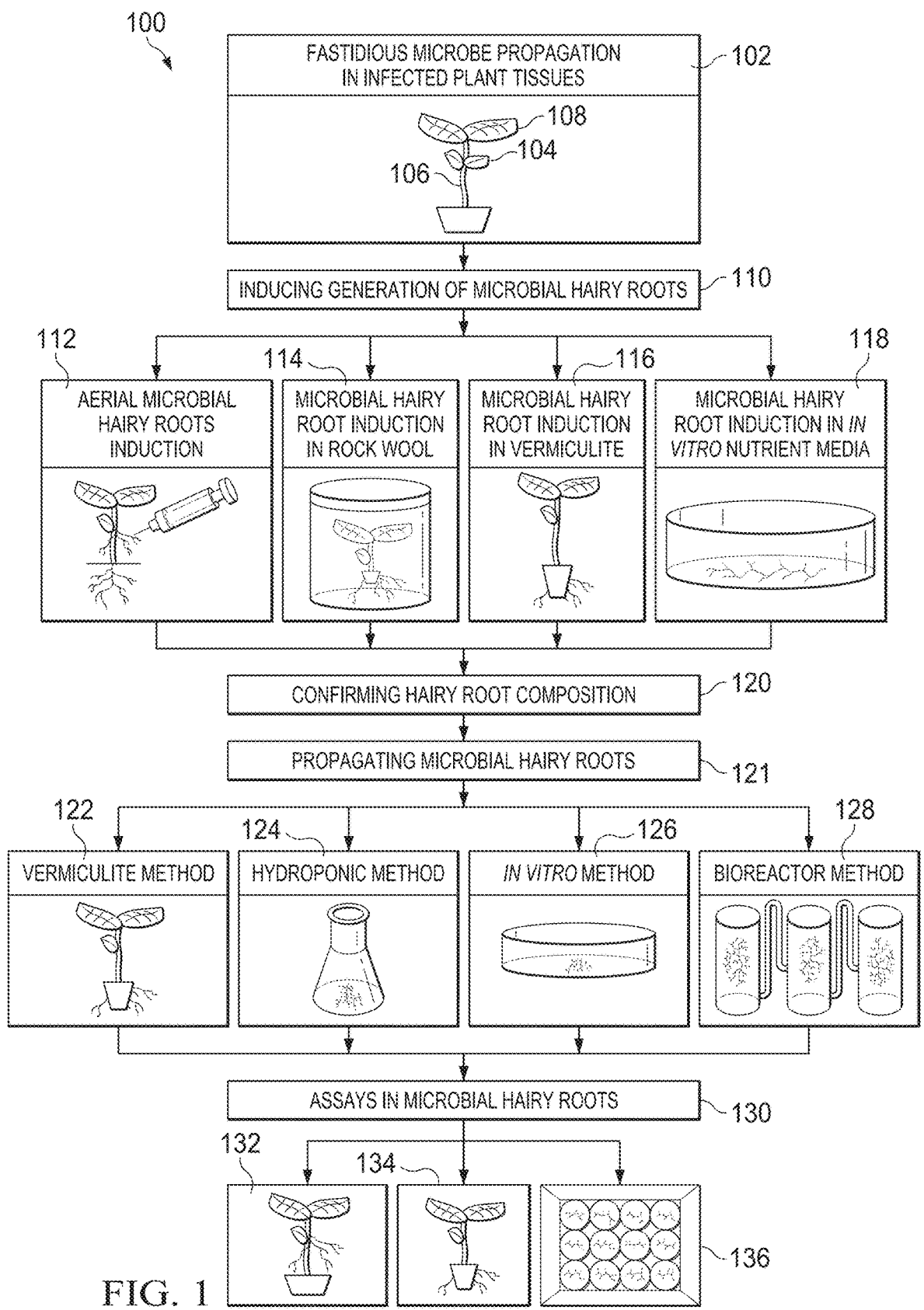

Despite the huge economic significance of fastidious microbes (e.g., plant pathogens), little is known of their biology, genetics, and the vector-pathogen-plant interactions. This knowledge may enable development of effective disease and pest management strategies to limit yield losses (e.g., tremendous losses). One bottleneck (e.g., a major bottleneck) in characterizing these fastidious microbes is their inability to grow outside their natural hosts, as they are obligate parasites of plants. It is estimated that >99% of microorganisms from any environment are non-cultivable in the laboratory. Numerous attempts have been made to create suitable artificial growth media and culture conditions for cultivating fastidious microbes; however, to date these approaches have had only limited success.

Plant hairy roots can be readily induced from diverse plant tissues upon infection by a soil bacterium, *Rhizobium rhizogenes* (recently revised from *Agrobacterium rhizogenes*). In a manner similar to its related cousin, *A. tumefaciens*, *R. rhizogenes* introduces its root-inducing (Ri) transfer-DNA (Ri-DNA plasmid), which encodes the root locus (rol) genes (e.g., rolB, rolC) into the plant genome. The expression of rol genes in planta overproduces the plant hormone, auxin, and induces hairy root initiation and proliferation.

Hairy airy roots are anatomically, morphologically, and metabolically similar to normal roots. Hairy roots are connected to a plant tissue from which they are generated by Intact xylem and phloem vasculature, thereby allowing continued transport of water, nutrients, cellular signaling—and as shown here fastidious microbes—through the vasculature. Typically hairy roots are smaller in diameter than a plant tissue from which they derive (e.g., stem, root) and are often numerous. A large number of plant genuses may be transformed by *R. rhizogenes* and generate hairy roots, including but not limited to: *Citrus* (e.g., lemon), Solanaceae (e.g., potato, tomato), *Daucus* (e.g., carrot), *Taxus, Cinchona, Gmelina, Glycine* (e.g., soybean), Rutaceae (e.g., Bael tree), Nyctaginaceae, and Rosaceae (e.g., apple).

The present disclosure relates, in some embodiments, to a method of cultivating a fastidious microbe (e.g., in vitro, in planta). The present disclosure relates, in some embodiments, to a hairy root system that may be directly used to cultivate and characterize fastidious microbes. The present disclosure relates, in some embodiments, to a hairy root system that may be used for high-throughput functional genetic and genomic studies of the fastidious microbe-plant interactions. In some embodiments, a hairy root system may be used for chemical genetic screens (e.g., screening antibiotics, essential oils, oxylipins) to combat devastating plant diseases. According to some embodiments, a hairy root system may include a genetically modified plant and may be beneficial in identifying gene related susceptibility and/or resistance to fastidious microbes in plant species.

According to some embodiments, *Rhizobium rhizogenes*-mediated hairy root cultures of a host plant (e.g., tomato, potato, pepper, citrus) may be infected with a fastidious microbe (e.g., *Candidatus* spp., *Xylella* spp., *Clavibacter* spp.). Explant source material may include any desired organ or tissue of a plant including, for example, cotyledons, hypocotyls, immature and mature shoots and roots). An optimal source may be identified for a particular set of conditions by testing multiple infected plant tissues. Hairy root multiplication techniques (e.g., techniques for scalability and/or multiplexing) may be included for high-throughput diagnostics and/or molecular characterization, according to some embodiments. Functional characterization for a hairy-root system may include, in some embodiments, genetic gain-of-function (e.g., overexpression) and loss-of-function (e.g., clustered, regularly interspaced, short palindromic repeat-associated (CRISPR/Cas), Transcription activator-like effector nuclease (TALEN) and Ribonucleic Acid inference (RNAi) knockdown) studies of candidate plant and pathogen-encoded genes. Gene constructs (e.g., representative gene constructs) or gene libraries may be transiently delivered into established hairy-roots by any desired method including, for example, vacuum infiltration and/or by DNA bombardment. In some embodiments, gene constructs may be inserted into the *R. rhizogenes* T-DNA prior to hairy-root induction, thus completing the process in a single step.

According to some embodiments, a hairy root system may be used for propagation and functional studies of any desired plant-microbe association (e.g., beyond vascular-colonizing phytobacteria) including viruses (e.g., Tomato spotted wilt virus, Cucumber mosaic virus, Cauliflower mosaic virus, Turnip yellow mosaic virus) , viroids (e.g., Potato spindle tuber viroid, Tomato apical stunt viroid, *Citrus* exocortis viroid), and endophytic microbes (e.g., *Acidovorax facilis, Azoarcus* sp. BH72, *Azospirillum* sp. B510, *Fusarium* spp., *Colletotrichum* spp, *Curvularia* spp., *Beauveria bassiana, Lecanicillium* spp, *Pythium oligandrum*).

Previous studies have not reported the application of hairy roots to culture or to the study of fastidious plant microbes. Thus, the present disclosure showing that hairy roots can support the growth of fastidious microbes may have a significant impact on large-scale propagation of microbial hairy roots for high-throughput applications. The disclosed hairy root system resolves a significant bottleneck in culturing and propagating fastidious phytopathogens and may result in the initiation of numerous biological studies of fastidious plant pathogens. Such studies offer the promise of new transformative developments in plant disease and pest management, as well as, agriculture in general.

The present disclosure, in some embodiments, may help establish and optimize *Candidatus Liberibacter* spp. microbial hairy root cultures in any suitable plant such as potato, tomato and citrus, and allow researchers to perform genetic and/or chemical analysis using the disclosed microbial hairy root system.

According to some embodiments disclosed here, hairy roots induced directly from infected plants may provide an easy, rapid, and scalable platform to culture and characterize fastidious vascular-colonizing plant pathogens. For example, Lso and Las are prevalent in South Texas and infect several Solanaceous crops including potato, tomato, and *Citrus* spp. Thus, Las-infected citrus trees in South Texas may be used to obtain Las-infected plant material. Plant tissues from Las-infected citrus trees may be collected and tested for Las presence by polymerase chain reaction (PCR) amplification of 16S rDNA, an established DNA marker for detecting Las. Las-positive citrus tissues may be further used as an explant source for microbial hairy root induction.

The present disclosure relates, in some embodiments, to a biological mimic hairy root platform for rapid culture, propagation, and functional studies of fastidious vascular-colonizing microbes (e.g., plant pathogens). Fastidious vascular-colonizing plant pathogens such as *Candidatus* spp., *Xylella* spp., viruses, phytoplasmas and spiroplasmas result in billions of dollars of annual crop losses. The inability to culture these and other vascular-limited microbes (e.g., pathogens) presents a tremendous challenge to researchers attempting to study these organisms. Plant hairy roots induced by *Rhizobium rhizogenes* are organized, stable tissues anatomically and metabolically similar to roots, and they possess intact xylem and phloem vasculature. According to some embodiments, microbe-containing hairy roots induced directly from infected plants may provide an easy, rapid, and scalable platform to culture, propagate, and characterize fastidious vascular-limited plant pathogens (e.g., in the laboratory).

According to some embodiments, *Candidatus Liberibacter* spp. microbial hairy root cultures in a plant (e.g., potato, tomato, citrus) may enable genetic analysis using a microbial hairy root system. In addition to alleviating previous challenges of culturing fastidious vascular-limited plant pathogens, a hairy root platform may be readily exploited for transformative, high-throughput functional studies including but not limited to genetic and chemical screens for novel antimicrobials and bactericides. Because *R. rhizogenes* may effectively induce hairy roots in diverse monocot and dicot plants, microbial hairy root systems, methods, and compositions for microbial cultivation may be applied to other agronomic crops and plant microbe associations beyond vascular-colonizing phytobacteria such as fungi, viruses, viroids, and endophytic microbes.

Generating an Explant and/or Inoculum Source

Insect vectors may spread fastidious microbes from plant to plant. Plant material colonized by a fastidious microbe (e.g., explant) may be generated, according to some embodiments, by allowing or introducing an insect vector carrying the fastidious microbe to feed upon a plant and thereby transferring the fastidious microbe to the plant tissue. Once transferred into a plant vascular system, a fastidious microbe can colonize and replicate.

According to some embodiments, a fastidious microbe carrying insect vectors may be collected from an environment (e.g., agricultural fields) and tested to determine whether they carry the fastidious microbe (e.g., 16S rDNA PCR). Insect vectors (e.g., fastidious microbe carrying insect vectors, non-carrying insect vectors) may be maintained (e.g., in insect cages) and propagated, in some embodiments. A fastidious microbe carrying insect vector, in some embodiments, may be generated in a laboratory setting, for example, by allowing a non-carrying insect vector to feed upon plant tissue infected by a fastidious microbe. Numerous methods are known for transmitting a fastidious microbe to an insect vector, as well as, maintaining and propagating an insect vector population, all of which are within the scope of the present disclosure.

In some embodiments, an insect vector population may be tested for the presence or absence of colonization by a fastidious microbe. Any suitable technique may be used to test an insect vector for the presence or absence of colonization by a fastidious microbe, for example 16S rDNA PCR. At least one fastidious microbe carrying insect vector may be permitted to feed upon an uninfected plant for a period of time (e.g., seven days); thereby transferring at least one fastidious microbe to the plant vasculature. Within the scope of this disclosure, numerous methods may be used to successfully transfer at least one fastidious microbe to a plant vasculature. Such methods may vary depending upon at least: the species and developmental stage of an insect vector, a level of fastidious microbe within an insect vector, a rate at which a fastidious microbe replicates within an insect vector, and a species and developmental stage of an uninfected plant. According to some embodiments, after a designated feeding period (e.g., seven days), a microbe carrying insect vector may be removed from the plant and the plant may be monitored for colonization and/or disease development. In some embodiments, disease symptoms may indicate colonization by a fastidious microbe. Any number of standard laboratory procedures may be used to identify the presence or absence of a fastidious microbe within a plant tissue. According to some embodiments, plant tissue may be tested for the presence or absence of fastidious microbe populations using 16S rDNA PCR. A plant or plant tissue (e.g., cotyledon) which tests positive for the presence of a fastidious microbe (e.g., PCR positive) may be used as a source of explant for microbial hairy root induction, according to some embodiments. According to some embodiments, a method for cultivating a fastidious plant microbe may include colonizing a plant with a fastidious microbe to generate an explant source. In some embodiments, colonizing a plant with a fastidious microbe may include exposing one or more surfaces of the plant to at least one fastidious microbe carrying insect vector (e.g., an Lso carrying psyllid). An explant, in some embodiments, may include a plant tissue, such as a cotyledon, a hypocotyl, an immature shoot, an immature root, a mature shoot, a mature root, or any combination thereof.

A Microbial Hairy Root Platform

FIG. 1 illustrates a microbial hairy root platform workflow 100 including: propagating a fastidious microbe in one or more plant tissues 102; inducing microbial hairy root production from infected plant tissues 110; propagating microbial hairy roots 120, and applying microbial hairy roots to downstream studies and applications 130, according to example embodiments of the present disclosure.

As shown in FIG. 1, according to some embodiments, a fastidious microbe may be propagated in one or more plant tissues 102. One or more plant tissues of an infected plant may be colonized by a fastidious microbe including a cotyledon 104, a hypocotyl 106, a leaf 108, an immature shoot, an immature root, a mature shoot, a mature root, or any combination thereof. Propagating a fastidious microbe (e.g., Lso, Las) in one or more plant tissues may include exposing a healthy plant to one or more vector species (e.g., psyllid) that are colonized by the fastidious microbe and that are known to feed on plant tissues, according to some embodiments. According to some embodiments, propagating a fastidious microbe may include various methods of asexual plant propagation. According to some embodiments, propagating a fastidious microbe may include identifying infected plants from an environment and maintaining the identified plants.

A microbial hairy root platform workflow 100, may include inducing microbial hairy root generation from an infected plant or plant tissue 110. According to some embodiments, inducing microbial hairy root generation may include culturing *Rhizobium rhizogenes*. Numerous methods are appropriate for culturing *R. rhizogenes* and are encompassed by this disclosure. Culturing *R. rhizogenes* may include growing *R. rhizogenes* in any appropriate culture medium (e.g., Luria-Bertani medium (LB)) to any appropriate optical density (e.g., 0.3). In some embodiments, a culture of *R. rhizogenes* may be grown to an O.D. of about 0.2, or about 0.3, or about 0.4, or about 0.5, or about 0.6. According to some embodiments, a culture of *R. rhizogenes* may be grown to an O.D. between 0.2 and 0.6, or between 0.3 and 0.6, or between 0.2 and 0.4. Upon reaching an elected optical density, a culture of *R. rhizogenes* may be removed from a medium (e.g., via centrifugation) and resuspended in a volume of plant culture medium (e.g., ½ MS, ½ B5+3% sucrose) or water (e.g., sterile water) to a desired concentration. In some embodiments, a culture of *R. rhizogenes* may be resuspended at an O.D. of about 0.2, or about 0.3, or about 0.4, or about 0.5, or about 0.6. According to some embodiments, a culture of *R. rhizogenes* may be resuspended at an O.D. between 0.2 and 0.6, or between 0.3 and 0.6, or between 0.2 and 0.4.

According to some embodiments, a strain of *R. rhizogenes* may be selected based on specific characteristics. For example, different *R. rhizogenes* strains may have varying potentials to induce hairy roots from plants. A suitable strain for propagating microbial hairy roots in a plant or explant (e.g., tomato, potato, citrus) may be empirically determined, in some embodiments, based on, for example, a percent induction of hairy roots in a selected explant tissue type and/or plant species (e.g., tomato, potato, citrus). Suitable strains of *R. rhizogenes* for evaluation and/or use may include, in some embodiments, American Type Cell Culture (ATCC) 15834, ATCC 43056, ATCC 43057, ATCC 1333, K599, or any combination thereof. According to some embodiments, for each combination of explant tissue and *R. rhizogenes* strain, induction efficiency may be determined by measuring parameters such as the following: (a) hairy root induction percentage per total explants; (b) hairy root initiation days per total explants; (c) hairy root induction frequency per single explant, and (d) fastidious microbe (e.g., Las and Lso) populations in the hairy roots. For accurate comparison of microbial titers amongst different samples (e.g., explant tissue type, plant species type), quantitative PCR techniques (e.g., q-PCR, quantitative Real-Time PCR) may be used, according to some embodiments. Statistical analysis, such as an analysis of variance (ANOVA) and Student's T-test, may be employed to determine significant differences between populations amongst different samples.

As illustrated in FIG. 1, both in planta 110, 112, 114 and in vitro 116 approaches may be used to induce microbial hairy root generation directly from one or more infected plant tissues. In planta approaches for inducing microbial hairy root generation include aerial induction of microbial hairy roots 110, rock wool induction of microbial hairy roots 112, and vermiculite induction of microbial hairy roots 114.

In Planta Methods of Inducing Microbial Hairy Roots

Inducing microbial hairy root generation 110, in some embodiments, may include selecting an infected plant (e.g., Lso) and preparing one or more surfaces of the infected plant (e.g., surface sterilization, wounding). Preparing an infected plant may include surface sterilization of one or more surfaces of the infected plant. Any appropriate surface sterilization techniques may be used including, in some embodiments, exposure of one or more surfaces of an infected plant for a designated period of time (e.g., 1 to 10 minutes) to a solution containing an alcohol (e.g., 70% ethanol), NaClO (bleach) (e.g., 2%, 10%), a non-phytotoxic anti-fungal (e.g., amphotericin B), an anti-bacterial (e.g., 200 mg/L cefotaxime or 100 mg/L carbenicillin) compound, or any combination thereof.

According to some embodiments, preparing an infected plant (e.g., colonized by Lso or Las) may include wounding one or more surfaces of the infected plant. Any suitable tools may be used to wound one or more surfaces of an infected plant, including scissors, a scalpel, forceps (e.g., fine gauge), a syringe, a needle, or any combination thereof. Wounded and exposed surfaces of an infected plant may serve as active sites for *R. rhizogenes* transformation and hairy root induction, in some embodiments.

In some embodiments, inducing microbial hairy root generation 110 may include contacting an infected plant or a portion of an infected plant with at least one *R. rhizogenes* cell (in planta approach), as shown in FIGS. 1 at 112, 114, and 116. Contacting an infected plant with at least one *R. rhizogenes* cell may include directly exposing one or more parts (e.g., a wound site) of an infected plant to a *R. rhizogenes* suspension (e.g., O.D. 0.3) (e.g., to generate aerial hairy roots) or vacuum infiltrating one or more parts of an infected plant with a *R. rhizogenes* suspension, according to some embodiments.

According to some embodiments, one or more portions of an infected plant may be directly contacted by a suspension containing at least one cell of *R. rhizogenes* (e.g., O.D. 0.3). Various methods may be used to contact one or more portion of an infected plant with a suspension containing at least one cell of *R. rhizogenes*. According to some embodiments, contacting one or more portions of an infected plant may include: applying a suspension containing at least one cell of *R. rhizogenes* to a wound site (e.g., using a dropper), dipping a fine needle in a suspension of *R. rhizogenes* and using the fine needle to wound one or more locations on an infected plant; injecting a suspension of *R. rhizogenes* into an infected plant using a syringe. As shown in FIG. 1 112, contacting an infected plant at a location above soil level may generate one or more aerial microbial hairy roots.

According to some embodiments, contacting one or more portions of an infected plant with at least one cell of *R. rhizogenes* (e.g., an exposed wound site) may include wrapping or covering (e.g., with aluminum foil) a contact site. Wrapping or covering a contact site may reduce exposure to light and/or maintain desired humidity levels, in some embodiments.

In some embodiments, contacting one or more portions of an infected plant with at least one cell of *R. rhizogenes* may include infiltrating the one or more portions of the infected plant using vacuum pressure. As shown in FIG. 1 at 116, inducing microbial hairy root generation may include removing a portion of an infected plant (e.g., a shoot) to form a wound site and contacting the wound site with a solution containing at least one cell of *R. rhizogenes* (e.g., O.D. 0.3). In some embodiments, contacting a portion of an infected plant with a solution containing at least one cell of *R. rhizogenes* (e.g., O.D. 0.3) may include submerging a wound site in the solution and exposing the portion of the infected plant to a vacuum environment for a period of time. Any vacuum environment that permits infiltration of at least one plant cell with at least one cell of *R. rhizogenes* may be used. In some embodiments, a vacuum environment may be about 20 inHg, or about 25 inHg, or about 30 inHg. According to some embodiments, a period of time for which a vacuum environment may any suitable length of time that permits infiltration of at least one plant cell with at least one cell of *R. rhizogenes*. A period of time for which a vacuum may be held may be any length of time. For example, in some embodiments, a vacuum may be held for at least about 30 sec, or at least about 1 min, or at least about 5 min, or at least about 10 min, or at least about 30 min, or at least about 60 min, or at least about 3 hours, or at least about 6 hours, or at least about 12 hours.

According to some embodiments, and as shown at 114 of FIG. 1, following vacuum infiltration a wound site may be removed from a solution of *R. rhizogenes* and covered by (e.g., completely covered, partially covered) inserting in a vermiculite matrix. In some embodiments, inducing microbial hairy root generation may include removing a portion of an infected plant (e.g., a shoot) to form a wound site, contacting the wound site with a solution containing at least one cell of *R. rhizogenes* (e.g., O.D. 0.3), removing the wound site from the solution, and covering the wound site with a vermiculite matrix. In some embodiments, a portion of an infected plant covered by a vermiculite matrix may be maintained in conditions suitable for formation of one or more microbial hairy roots. A vermiculite matrix may be periodically changed, in some embodiments.

As shown in FIG. 1 at 114, inducing microbial hairy root generation may include removing a portion of an infected plant (e.g., a shoot) to form a wound site, covering the wound site in a rock wool matrix, and exposing the rock wool matrix to a solution containing at least one cell of *R. rhizogenes*. Exposing a rock wool matrix to a solution containing at least one cell of *R. rhizogenes* (e.g., O.D. 0.3) may include providing a sufficient volume of the solution to partially saturate or fully saturate the rock wool matrix. According to some embodiments, a portion of an infected plant covered by a rock wool matrix may be maintained in conditions suitable for co-cultivation of the *R. rhizogenes* with one or more plant cells for a co-cultivation period. According to some embodiments, a co-cultivation period may be at least about 12 hours, or at least about 24 hours, or at least about 48 hours, or at least about 72 hours. Following a co-cultivation period, in some embodiments, a rock wool matrix may be dried (e.g., air dried, vacuum dried) to form a dried rock wool matrix. A dried rock wool matrix may retain some moisture, according to some embodiments. In some embodiments, a dry rock wool matrix may have a reduced population of *R. rhizogenes* when compared to the same rock wool matrix prior to drying. According to some embodiments, drying a rock wool matrix may be performed by exposing the rock wool matrix to one or more drying conditions (e.g., temperatures, air currents) for a period of at least 6 hours, or at least 12 hours, or at least 24 hours, or at least 36 hours, or at least 48 hours, or at least 72 hours. In some embodiments, a dried rock wool matrix may be rehydrated.

Contacting one or more portions of an infected plant (e.g., 112, 114, 116) with at least one cell of *R. rhizogenes* may include maintaining a contacted plant in conditions appropriate for formation of microbial hairy roots (e.g., incubator, growth chamber, greenhouse) until at least one hairy root generates. Conditions appropriate for generation of one or more microbial hairy roots may vary depending upon factors including: a species of infected plant, a portion of an infected root contacted, a method of contacting an infected plant, a strain of *R. rhizogenes* selected, a concentration of *R. rhizogenes* in a contact solution, or any combination thereof. According to some embodiments, an infected plant may be maintained at a temperature of between about 21° C. and about 25° C. In some embodiments, an infected plant may be maintained in conditions having a light/dark cycle of about 8 hours of light to about 16 hours of light per 24 hour period, according to some embodiments. In some embodiments microbial hairy roots may appear about 10 to 21 days after contacting an infected plant with a suspension of *R. rhizogenes*.

In vitro Methods of Inducing Microbial Hairy Roots

As illustrated in FIG. 1 at 118, inducing microbial hairy root generation may be performed in vitro, according to some embodiments of the present disclosure. In vitro induction of microbial hairy roots, according to some embodiments, may include: preparing a culture of *R. rhizogenes*, preparing an explant, contacting (e.g., co-cultivation) the explant with a solution containing at least one *R. rhizogenes* cell, and exposing the explant to one or more selective conditions.

According to some embodiments, in vitro methods 118 of inducing microbial hairy root generation 110 may include selecting one or more infected tissues (e.g., leaf, cotyledon, hypocotyl, and/or root) from a plant colonized by a fastidious microbe to serve as an explant. In some embodiments, inducing microbial hairy root generation may include preparing an explant (e.g., surface sterilization, wounding). Preparing an explant may include surface sterilization of one or more surfaces of the explant (e.g., a cotyledon). Any appropriate surface sterilization techniques may be used including, in some embodiments, exposure of one or more surfaces of an infected plant or an explant to a solution containing an alcohol (e.g., 70% ethanol), NaClO (bleach) (e.g., 2.5%, 10% solution), a non-phytotoxic anti-fungal (e.g., amphotericin B), an anti-bacterial (e.g., cefotaxime or carbenicillin) compound, or any combination thereof for a designated period of time (e.g., 1 to 10 minutes).

In some embodiments, preparing an explant (e.g., a cotyledon) may include cutting an explant into smaller pieces (e.g., about 2 centimeter (cm) long)), wounding at least one portion of an explant (e.g., using forceps), or any combination thereof. Any suitable tools may be used to prepare an explant, including scissors, a scalpel, forceps (e.g., fine gauge), a syringe, a needle, or any combination thereof. Wounded and exposed surfaces of an explant (e.g., a cotyledon) may serve as active sites for R. rhizogenes transformation and hairy root induction.

In some embodiments, inducing microbial hairy root generation may include contacting (e.g., co-cultivating) an explant (e.g., a surface sterilized and wounded cotyledon) with at least one R. rhizogenes cell (in vitro approach) 116. Contacting an explant (e.g., a prepared explant) with at least one cell of R. rhizogenes may include immersing the explant or prepared explant in a suspension containing at least one cell of R. rhizogenes (e.g., OD 0.3) for a period of time (e.g., 20 min), in some embodiments. An explant may be immersed in a suspension containing at least one cell of R. rhizogenes for any period of time, for example for at least 1 min, or for at least 5 min, or for at least 10 min, or for at least 15 min, or for at least 20 min, or for at least 25 min, or for at least 30 min, according to some embodiments. In some embodiments, contacting (e.g.,) co-cultivating an explant may include immersing an explant (e.g., a prepared explant) in a suspension containing at least one cell of R. rhizogenes (e.g., O.D. 0.3) for a period of about 1 min to about 30 min, or about 5 min to about 25 min, or about 10 min to about 25 min, or about 15 min to about 25 min, or about 15 min to about 20 min In some embodiments, contacting an explant with at least one cell of R. rhizogenes may include transferring an explant from a suspension containing at least one cell of R. rhizogenes (e.g., O.D. 0.3) to a co-cultivation medium (e.g., ½ MS, ½ B5+3% sucrose)and incubating the explant for a period of at least 12 hours, or at least 24 hours, or at least 36 hours, or at least 48 hours, or at least 72 hours. Incubating an explant or prepared explant may be performed under any suitable conditions for the survival of both the explant and the R. rhizogenes. In some embodiments, incubating an explant may be performed at a temperature of about 21° C., or about 22° C., or about 23° C., or about 24° C., or about 25° C. According to some embodiments, incubating an explant may be performed at a temperature of about 21° C. to about 25° C. A co-cultivation medium may include any medium that permits growth of R. rhizogenes, for example: a ½ MS, ½ B5+3% sucrose medium.

According to some embodiments, contacting an explant may include immersing the explant in a suspension containing at least one cell of R. rhizogenes for a period of 20 min, transferring the explant to a co-cultivation medium of ½ MS, ½ B5+3% sucrose, and incubating the explant at a temperature of 21° C. to 25° C. for a period of 72 hours.

In some embodiments, following contacting and incubation an explant may be exposed to one or more selective conditions. According to some embodiments, an explant or prepared explant may be transferred from a co-cultivation medium to selection medium. A selection medium may be any medium that inhibits (e.g., reduce a concentration or growth of) R. rhizogenes, untransformed tissue, untransformed roots, or any combination thereof. According to some embodiments, a selection medium may inhibit a population of R. rhizogenes but not inhibit a fastidious microbe (e.g., Lso). According to some embodiments, various measures may be used to avoid the potential pitfall of using common antibiotics (e.g., cefatoxime, carbencillin and kanamycin). For example, some antibiotics may inhibit a fastidious microbe residing inside an explant. Therefore, in some embodiments, alternative antibiotics, such as streptomycin (e.g., at 200 mg/L concentration), neomycin (e.g., at 100 mg/L), penicillin (e.g., at 100 mg/L) and hygromycin (e.g., at 100 mg/L), that are phloem-immobile and/or non-phytotoxic may be used. An explant may be transferred from a co-cultivation medium (e.g., about ½ MS, ½ B5+3% sucrose) to a selection medium (e.g., about ½ MS, ½ B5+3% sucrose+200 mg/L cefotaxime or 100 mg/L carbenicillin) which may inhibit (e.g., reduce a concentration or growth of) R. rhizogenes.

According to some embodiments, following contacting and incubation an explant may be exposed to osmotic stress. Exposing an explant to osmotic stress may be effective in inhibiting R. rhizogenes (e.g., reduce a concentration of). Various methods exist for exposing an explant to osmotic stress. For example, an explant may be exposed to osmotic stress by repeatedly rinsing the explant in sterilized de-ionized water for a period of time (e.g., about 30 minutes). In some embodiments, de-ionized water used for exposing an explant to osmotic stress may include an antibiotic compound, for example, 200 mg/L cefotaxime or 100 mg/L carbenicillin.

After contacting and exposing an explant to one or more selective conditions, an explant may be placed in an appropriate growing environment (e.g., incubator, growth chamber, greenhouse) until at least one hairy root generates. An explant may be subsequently monitored for hairy root induction. Depending on a plant species, an explant source, and a R. rhizogenes strain used, hairy roots may emerge within two to four weeks, according to some embodiments.

Microbial Hairy Root Induction Efficiency

In some embodiments, a hairy root induction efficiency may vary (e.g., significantly vary) based on various factors including: plant variety, strain of R. rhizogenes, and/or explant source (e.g., a cotyledon, a hypocotyl, an immature shoot, an immature root, a mature shoot, and a mature root). Empirical data may be used to optimize hairy root induction efficiencies. For accurate comparison of microbial populations amongst different samples (e.g., explant tissue type, plant species type), quantitative PCR techniques (e.g., q-PCR, quantitative Real-Time PCR) may be used, according to some embodiments. Statistical analysis, such as an analysis of variance (ANOVA) and Student's T-test, may be employed to determine significant differences between populations amongst different samples.

According to some embodiments, hairy root induction efficiencies may range from about 10% to about 90% depending on the plant variety, explant tissue, and R. rhizogenes strain used. The preferred explant tissue and R. rhizogenes strain may maximize microbial hairy root induction efficiency in various plants such as citrus, tomato, and potato.

Confirmation of a Hairy Root

As shown in FIG. 1 at 120, a microbial hairy root platform workflow 100, may include confirming that a microbial hairy root (e.g., generated in plant or in vitro) was induced by transformation by R. rhizogenes. Various molecular methods may be used in confirming that a microbial hairy root (e.g., generated in plant or in vitro) was induced by transformation by R. rhizogenes. For example, according to some embodiments, PCR amplification of known root inducing (Ri) DNA genes (e.g., rolB, rolC) may be conducted to confirm that a microbial hairy root (e.g., generated in planta or in vitro) was induced by transformation by R. rhizogenes.

Confirmation of Colonization of a Hairy Root by a Fastidious Microbe

A microbial hairy root platform workflow 100, may include confirming that a microbial hairy root generated from an infected plant is colonized by the fastidious microbe (e.g., Lso, Las), as shown in FIG. 1 at 120. Numerous scientific methods may be used to confirm that a microbial hairy root from an explant or an infected plant is colonized by a fastidious microbe without deviating from this disclosure, including but not limited to PCR, q-PCR, quantitative Real-Time PCR, reverse-transcription qPCR, enzyme-linked immunosorbent assay (ELISA), or any combination thereof.

Propagation of Microbial Hairy Roots Colonized by a Fastidious Microbe

According to some embodiments, a microbial hairy root platform workflow 100, may include propagating microbial hairy roots for downstream studies and applications. To successfully utilize microbial hairy roots for high-throughput biological studies, it may be desirable to propagate a microbial hairy root inoculum in sufficiently large quantities, according to some embodiments. Hairy roots systems are amenable to large-scale propagation. According to some embodiments, a harvested hairy root may be clonally propagated. Clonal propagation of a harvested hairy root may provide an increased source of a fastidious microbe contained within a harvested hairy root (e.g., a microbial hairy root inoculum). According to some embodiments of the disclosure, propagating microbial hairy roots may be performed using a vermiculite method 122, a hydroponic method 124, an in vitro media method 126, a bioreactor method 128, or any combination thereof.

According to some embodiments, propagating microbial hairy roots may be performed when a microbial hairy root attached to an infected plant or an explant has reached a desired length. In some embodiments, propagating microbial hairy roots may be performed when a microbial hairy root attached to an infected plant or an explant has reached a length of at least about 1 cm, or at least about 1.5 cm, or at least about 2 cm, or at least about 2.5 cm, or at least about 3 cm, or at least about 3.5 cm, or at least about 4 cm, or at least about 4.5 cm, or at least about 5 cm.

As described above, there are multiple in planta approaches that may be used to generate one or more microbial hairy roots. Such in planta generated microbial hairy roots may still be attached to at least a portion of an infected plant capable of photosynthetic activity (i.e., an attached hairy root). According to some embodiments, propagating microbial hairy roots 121 may include exposing an attached hairy root to one or more selective conditions (e.g., prior to being propagated). Exposing an attached hairy root to one or more selective conditions may include exposing one or more surfaces of the attached hairy root to a solution containing an alcohol (e.g., 70% ethanol), NaClO (bleach) (e.g., 2.5%, 10%), a non-phytotoxic anti-fungal (e.g., amphotericin B), an anti-bacterial (e.g., cefotaxime, carbenicillin) compound, or any combination thereof for a designated period of time (e.g., 1 to 10 minutes), according to some embodiments. In some embodiments, exposing an attached hairy root to one or more selective conditions may include exposing the attached hairy root to osmotic stress. Exposing an attached hairy root to one or more selective conditions, in some embodiments, may include transferring the attached hairy root to a selection media (e.g., about ½ MS, ½ B5+3% sucrose+200 mg/L cefotaxime or 100 mg/L carbenicillin) to inhibit (e.g., reduce a concentration of) R. rhizogenes.

According to some embodiments, propagating microbial hairy roots 121 may include harvesting one or more microbial hairy roots from an explant, an infected plant, a portion of an infected plant, or an attached hairy root to form a harvested hairy root. Propagating microbial hairy roots 121 may include exposing a harvested hairy root to selective conditions which, in some embodiments, may reduce a concentration of R. rhizogenes. Exposing a harvested hairy root to one or more selective conditions may include exposing one or more surfaces of the harvested hairy root to a solution containing an alcohol (e.g., 70% ethanol), NaClO (bleach) (e.g., 2.5%, 10%), a non-phytotoxic anti-fungal (e.g., amphotericin B), an anti-bacterial (e.g., cefotaxime or carbenicillin) compound, or any combination thereof for a designated period of time (e.g., 1 to 10 minutes), according to some embodiments. In some embodiments, exposing a harvested hairy root to one or more selective conditions may include transferring a harvested hairy root to a selection media (e.g., about ½ MS, ½ B5+3% sucrose+200 mg/L cefotaxime or 100 mg/L carbenicillin). In some embodiments, exposing a harvested hairy root to one or more selective conditions may include exposing a harvested hairy root to osmotic stress. For example, a harvested hairy root may be exposed to osmotic stress by repeated rinsing in sterilized de-ionized water for a period of time (e.g., about 30 minutes).

As shown in FIG. 1 at 122, propagating microbial hairy roots may be performed using a vermiculite method 122. A vermiculite method 122, in some embodiments, may include transplanting an attached hairy root (e.g., a surface sterilized attached hairy root) into a vermiculite matrix. According to some embodiments, a vermiculite method 122 of propagating microbial hairy roots may include periodically transferring an attached hairy root to a fresh vermiculite matrix. A transplanted attached hairy root in a vermiculite matrix may be placed in suitable conditions for maintenance of a photosynthetic portion of the attached hairy root. For example, the vermiculite hairy roots may be propagated in a growth chamber with a diurnal cycle of 14 hour of light (intensity: 100 µmol m$^{-2}$s$^{-1}$), 10 hour dark, and 21° C. to about 25° C.

According to some embodiments, propagating microbial hairy roots may be performed using a hydroponic method 124. A hydroponic method 124 may include, according to some embodiments, placing an attached hairy root (e.g., exposed to osmotic stress) or a harvested hairy root (e.g., surface sterilized) in a nutrient rich medium (e.g., ½ MS, ½ B5+3% sucrose media) to generate a hydroponic culture. In some embodiments, a nutrient rich medium may include antibiotics or antifungal components. A hydroponic culture may be maintained at any appropriate conditions for growth of an attached hairy root or a harvested hairy root. In some embodiments, a hydroponic culture may be agitated. According to some embodiments, a hydroponic culture may be periodically supplemented with an additional nutritional source (e.g., a fresh media supply). A hydroponic culture, in some embodiments, may be maintained at a temperature of about 21° C. to about 25° C. According to some embodiments, supplying an external light source is unnecessary for growth of a hydroponic culture. As shown in FIG. 1 at 126, propagating microbial hairy roots may be performed using an in vitro media method 126. An in vitro media method 126 may include, according to some embodiments, placing an attached hairy root (e.g., exposed to osmotic stress) or a harvested hairy root (e.g., surface sterilized) on a plate of nutrient rich media (e.g., ½ MS, ½ B5+3% sucrose media) to generate an in vitro culture. In some embodiments, a nutrient rich medium may include antibiotics or antifungal components. An in vitro culture may be maintained at any appropriate conditions for growth of an attached hairy root or a harvested hairy root. According to some embodiments, an in vitro media method 126 may include periodically transplanting an attached hairy root or a harvested hairy root to a fresh plate of nutrient rich media. An in vitro culture, in some embodiments, may be maintained at a temperature of about 21° C. to about 25° C. According to some embodiments, supplying an external light source is unnecessary for growth of an in vitro culture.

As shown in FIG. 1 at 128, according to some embodiments, propagating microbial hairy roots may be performed using a bioreactor method 128. A bioreactor method 128 may include, according to some embodiments, placing an attached hairy root (e.g., exposed to osmotic stress) or a harvested hairy root (e.g., surface sterilized) in a bioreactor system containing a nutrient rich medium (e.g.,½ MS, ½ B5+3% sucrose media) to generate a bioreactor culture. In some embodiments, a nutrient rich medium may include antibiotics or antifungal components.

Various bioreactor systems may be used without deviating from the present disclosure. For example, in some embodiments, liquid-phase and/or gas-phase bioreactors may be used in a bioreactor method of propagating microbial hairy roots. According to some embodiments, an immersion system bioreactor or a temporary immersion system bioreactor (e.g., the SETIS system) may be used in a bioreactor method of propagating microbial hairy roots. In some embodiments, an attached hairy root or a harvested hairy root may be periodically immersed in a nutrient rich medium for a period of time calculated to allow sufficient uptake of nutrients (e.g., a temporary immersion system bioreactor). In some embodiments, a temporary immersion system may contribute to an improvement of gas exchange and avoidance of hypoxia/aeration issues when compared to an immersion system where plant tissues are perpetually immersed in a nutrient medium. A temporary immersion system (e.g., SETIS system) may be inexpensive, easy to establish, and/or scalable (e.g., highly scalable). Individual units of a temporary immersion system may be designed to function independently, in some embodiments. According to some embodiments, individual units of a bioreactor may be multiplexed such that a first bioreactor unit is attached to at least a second bioreactor unit. A multiplexed bioreactor set-up may reduce loss due to contamination when compared to a single bioreactor unit as contamination can be prevented from spreading from unit to unit.

A bioreactor culture may be maintained at any appropriate conditions for growth of an attached hairy root or a harvested hairy root. In some embodiments, a bioreactor culture may be aerated. According to some embodiments, a bioreactor culture may be periodically supplemented with an additional nutritional source (e.g., a fresh media supply). A bioreactor culture, in some embodiments, may be maintained at a temperature of about 21° C. to about 25° C. According to some embodiments, supplying an external light source is unnecessary for growth of a bioreactor hairy root culture.

According to some embodiments, propagating microbial hairy roots may be achieved in a relatively short period of time. In some embodiments, a microbial hairy root population may be generated from an infected plant or an explant to a propagated mass of microbial hairy roots in about six to ten weeks.

A Hairy-Root Genetic Screening System

As illustrated in FIG. 1 at 130, in addition to alleviating previous challenges of culturing fastidious vascular-limited plant microbes, a hairy root platform may be readily exploited for transformative, high-throughput functional studies including but not limited to genetic and chemical screens for novel antimicrobials and bactericides. Because *R. rhizogenes* may effectively induce hairy roots in diverse monocot and dicot plants, microbial hairy root systems, methods, and compositions for microbial cultivation may be applied to other agronomic crops and plant microbe associations beyond vascular-colonizing phytobacteria such as fungi, viruses, viroids, and endophytic microbes.

Assays may be performed using microbial hairy roots that remain attached to plant tissue, such as aerial hairy root shown in FIG. 1 at 132 or microbial hairy roots generated using a rock wool or vermiculite method as shown in FIG. 1 at 134, according to some embodiments. In some embodiments, assays may be performed using harvested microbial hairy roots, as shown in FIG. 1 at 136 where a multi-well assay is illustrated.

Microbial hairy root systems, methods, and compositions, according to some embodiments, may solve a long standing problem in plant pathology to culture fastidious microbes and/or enable transformative biological and genetic studies of the fastidious microbes. For example, a microbial hairy root system may be deployed for rapid screening of novel resistance genes, antimicrobial compounds, bactericides, etc. Such screening may help fight devastating diseases such as ZC and HLB. Microbial hairy roots can also be leveraged to better understand the interactions occurring between the host-pathogen-vector. Therefore, microbial hairy root systems, methods, and compositions disclosed herein may advance U.S. agriculture and plant disease management by aiding in developing control strategies of potentially-devastating fastidious plant pathogens.

A microbial hairy root platform and system disclosed herein may be integrated into programs towards identification of novel resistance genes and antimicrobial compounds. For example, the system may help achieve rapid functional and chemical genetic screening of candidate disease resistance genes and antimicrobial molecules (e.g., antibiotics, essential oils, oxylipins) in a plant (e.g., tomato, potato, citrus) microbial hairy root systems. Because *R. rhizogenes* may effectively induce hairy roots in diverse dicot and monocots, the disclosed principles may also establish microbial hairy root systems for other crops and plant microbe associations beyond vascular-limited phytobacteria, such as fungi, viruses, viroids, and beneficial endophytes. In some embodiments, a hairy root system may be used to study plant pathogens (e.g., economically important plant pathogens) and their corresponding diseases (e.g., zebra chip (ZC), HLB).

The present disclosure relates, in some embodiments, to a microbial hairy root platform for rapid culture, propagation, and functional studies of fastidious vascular colonizing plant microbes (e.g., pathogens). According to some embodiments, microbe-colonized hairy roots induced directly from colonized plants may provide an easy, rapid, and scalable platform to culture, propagate, and characterize fastidious vascular-limited plant microbes (e.g., in the laboratory).

According to some embodiments disclosed herein, genetic analysis (e.g., an analysis of transgene function) may be performed using a microbial hairy root system. In some embodiments, a hairy root system may comprise cultivating hairy root from a genetically modified plant by transforming the genetically modified plant with a strain of *R. rhizogenes*. For example, a plant that is genetically modified to overexpress a plant Broad-complex, Tramtrack and Bric-abrac (BTB) domain family protein, NPR1, or green florescent protein (GFP) may be transformed with a strain of *R. rhizogenes* to induce production of a hairy root. In some embodiments, a genetically modified plant transformed by *R. rhizogenes* may be colonized by a fastidious microbe (e.g., Las, Lso).

A hairy root system may comprise, in some embodiments, transforming a plant with a *R. rhizogenes* strain having one or more modified T-DNA plasmids. For example, in some embodiments, a modified *R. rhizogenes* may be formed. A modified *R. rhizogenes* may comprise one or more T-DNA plasmids, each encoding at least one of a target gene (e.g., NPR1, GFP), a CRISPR/Cas, a TALEN, or an RNAi construct, in some embodiments. According to some embodiments, a hairy root system may comprise transforming a plant with a *R. rhizogenes* strain having a first modified T-DNA plasmid and a second modified T-DNA plasmid, with each of the first T-DNA plasmid and the second T-DNA plasmid encoding at least one of a target gene, a CRISPR/Cas, a TALEN, or an RNAi construct. In some embodiments, a T-DNA plasmid may encode a library of target genes. Because *R. rhizogenes* can simultaneously transfer T-DNA and Ri-DNA into plant cells, transformation of a plant with a modified *R. rhizogenes* may result in production of a plant producing hairy roots that express (e.g., overexpress) at least one of a target gene, a CRISPR/Cas, a TALEN, or an RNAi construct.

According to some embodiments, one or more T-DNA plasmid encoding at least one of a target gene (e.g., NPR1, GFP), a CRISPR/Cas, a TALEN, or an RNAi construct, may be delivered transiently into a hairy root using mild vacuum infiltration or DNA bombardment; thereby forming a genetically modified hairy root.

In some embodiments, a T-DNA plasmid encoding at least one of a target gene (e.g., NPR1, GFP), a CRISPR/Cas, a TALEN, or an RNAi construct may further comprise a reporter/marker gene (e.g., GFP, β-glucuronidase [GUS], antibiotic resistance gene). Because the use of standard antibiotics for the induction and selection of microbial hairy roots is controlled, green fluorescent protein (GFP)-based or GUS-based screening may be used (e.g., optionally, exclusively) to identify microbial hairy roots harboring a modified T-DNA construct.

In some embodiments, transformation of a hairy root with at least one of a target gene (e.g., NPR1, GFP), a CRISPR/Cas, a TALEN, or an RNAi construct may be confirmed using reverse-transcription PCR (RT-PCR), PCR, DNA-sequencing, Southern blot analysis, northern blot analysis, and/or western blot analysis. Hairy roots co-transformed or infiltrated with an empty or GFP containing binary T-DNA vector may be used as a negative control. A person having skill in the art would understand that other methods of confirmation of transformation with a target gene may be used without deviating from the present disclosure.

Evaluation of at least one of a target gene (e.g., NPR1, GFP), a CRISPR/Cas, a TALEN, or an RNAi construct may include quantitative analysis of titers of a fastidious plant microbe colonizing a hairy root system. For example, a target gene that is involved in resistance mechanisms may have reduced titers of the fastidious plant microbe when compared to a colonized hairy root that does not contain the target gene. Evaluation of titers of a fastidious plant microbe may include qualitative or quantitative evaluations.

As an example, a hairy root system may be used to perform a genetic analysis of a NPR1, GFP gene. The Broad-complex, Tramtrack and Bric-abrac (BTB) domain family of proteins are well-conserved in plants and are involved in diverse plant signaling pathways. For example, a plant BTB protein, NPR1, may be modulated by diverse abiotic and biotic stress signals including salicylic-acid, methyl-jasmonate, reactive oxygen species, and wounding in Arabidopsis. Therefore, to evaluate the NPR1 gene's potential role in a response to a fastidious plant microbe (e.g., Lso, Las), a hairy root system may be used. For example, a potato, a tomato, and a citrus plant cultivated by their respective Lso or Las pathogen may be transformed with a *R. rhizogenes* strain having a T-DNA plasmid containing a NPR1 gene or a GFP gene. To determine the effect of NPR1 on Lso and Las, bacterial titers in the hairy roots overexpressing NPR1 may be quantified and compared to the control hairy roots expressing only GFP. For example, the resulting titers may indicate that expression (e.g., overexpression) of the NPR1 gene promoted resistance (or tolerance) to Lso and Las in the hairy roots. Together, these tests may provide rapid functional applications using the disclosed microbial hairy roots.

As will be understood by those skilled in the art who have the benefit of the instant disclosure, other equivalent or alternative compositions, devices, methods, and systems for cultivating fastidious plant pathogens can be envisioned without departing from the description contained herein. Accordingly, the manner of carrying out the disclosure as shown and described is to be construed as illustrative only.

Persons skilled in the art may make various changes in the nature, number, and/or arrangement of steps without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed systems, compositions, apparatuses, and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for cultivating a fastidious microbes may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Example 1

Generating an Explant and/or Inoculum Source

Figure 2A:
Figure 2B:
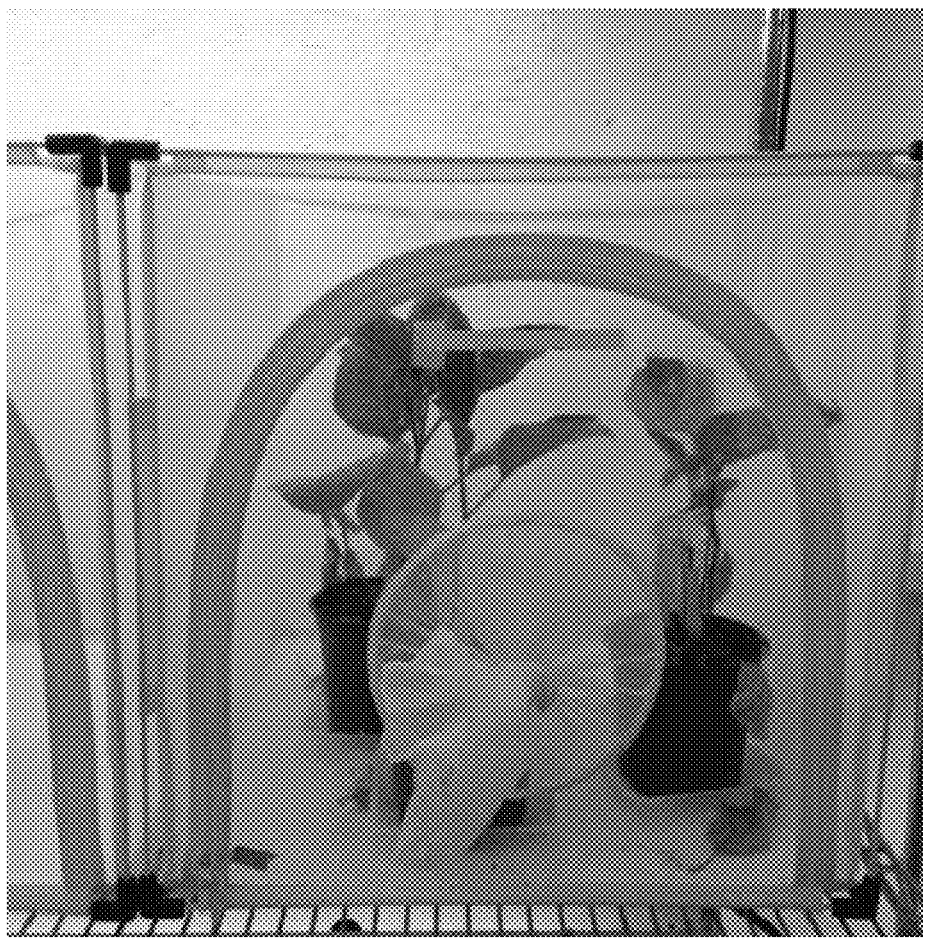

FIGS. 2A through 2G illustrate an example of using fastidious microbe carrying insect vectors to generate plants colonized by the fastidious microbe for use as explants in hairy root methods and systems. Specifically, FIGS. 2A and 2B illustrate Lso-carrying and Lso-free potato psyllid colonies (Central haplotype), maintained in insect cages at the Texas A&M AgriLife Center-Weslaco. The psyllids were originally collected from commercial potato fields near Dalhart, Tex. in 2007. As shown in FIG. 2A and FIG. 2B, the psyllids were fed on eggplants and kept at 25° C. with a 12:12 light:darkness (L:D) hour photoperiod and about 50% relative humidity in a controlled growth chamber. Periodically, a psyllid colony (e.g., Lso-carrying, Lso-free) was tested for the presence or absence of Lso colonization using 16S rDNA PCR.

Figure 2C:
Figure 2D:
Figure 2E:
Figure 2F:

To generate explant material, ten adult Lso-carrying psyllids were released into cages containing two-month to three-month-old potato and tomato plants and permitted to feed. As a control, ten Lso-free psyllids were released into a separate set of cages containing two-month to three-month-old potato and tomato plants and permitted to feed. After a period of three days, the psyllids were removed and foliar symptoms (chlorosis and necrosis) on the infected potato and tomato plants were monitored. As shown in FIG. 2D and 2F respectively, typical disease symptoms began to appear on the tomato and potato plants exposed to the feeding of Lso-carrying psyllids within two to four weeks after feeding. By contrast, those tomato (FIG. 2C) and potato (FIG. 2E) plants that were exposed to Lso-free psyllid feeding did not exhibit disease symptoms (FIG. 2C and FIG. 2E respectively).

Figure 2G:
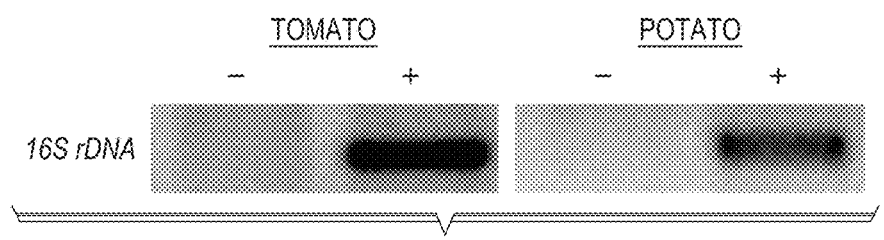

As shown in FIG. 2G, the presence of Lso in the infected plants (e.g., tomato in FIG. 2D and potato in FIG. 2F) was validated by PCR amplification of 16S rDNA. Plant material that tested positive for Lso infection was used as a source of explant (for in vitro approaches) and as a colonized plant (for in planta approaches) for microbial hairy root induction.

Example 2

Culturing *Rhizobium rhizogenes*

A fresh culture of *R. rhizogenes* was cultured to an optical density (OD) of about 0.3. The culture was pelleted by centrifugation and the *R. rhizogenes* cells were re-suspended in a sterile ½ MS or ½ B5+3% sucrose medium to an O.D. of 0.3.

Example 3

In vitro Induction of Microbial Hairy Roots

Figure 3A:
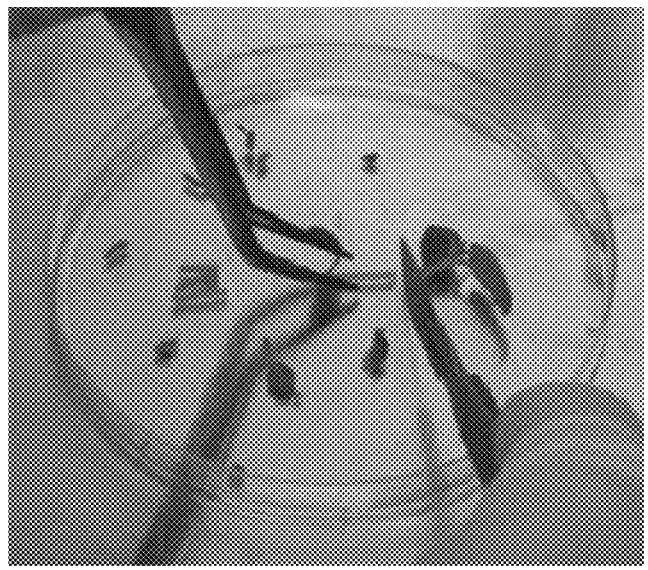

Portions of both healthy plants and plants colonized with Lso were harvested including cotyledon, hypocotyl, immature shoot, and immature root regions. The plant portions were surface sterilized using a solution containing 70% ethanol, 2.5% or 10% NaClO, and water. As shown in FIG. 3A, portions of the surface sterilized plants were cut using a scalpel into pieces having a length of about 2 cm each. Additionally, each of the pieces was gently wounded using a sterilized pair of fine forceps to generate prepared explants.

Figure 3B:
Figure 3C:
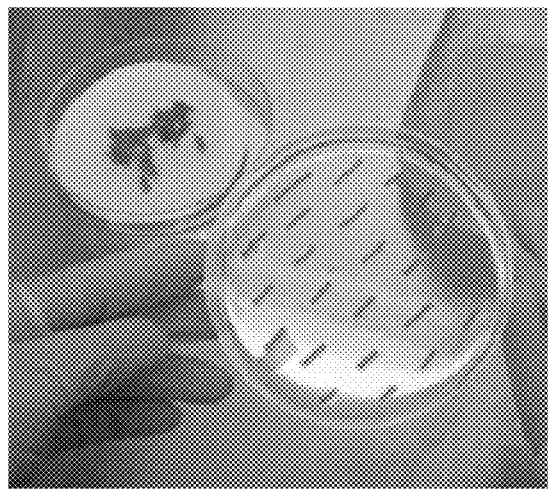

As shown in FIG. 3B, the prepared explants were contacted with a suspension of *R. rhizogenes* by immersion in a suspension prepared as described in Example 2. The immersed explants were agitated for a period of 20 min. As shown in FIG. 3C, the explants were then removed from the suspension of *R. rhizogenes* and placed on a plate of ½ MS or ½ B5+3% sucrose medium. The explants were incubated on plate for 72 hours at about 21-25° C. thereby allowing the explant and *R. rhizogenes* to co-cultivate.

Figure 3D:
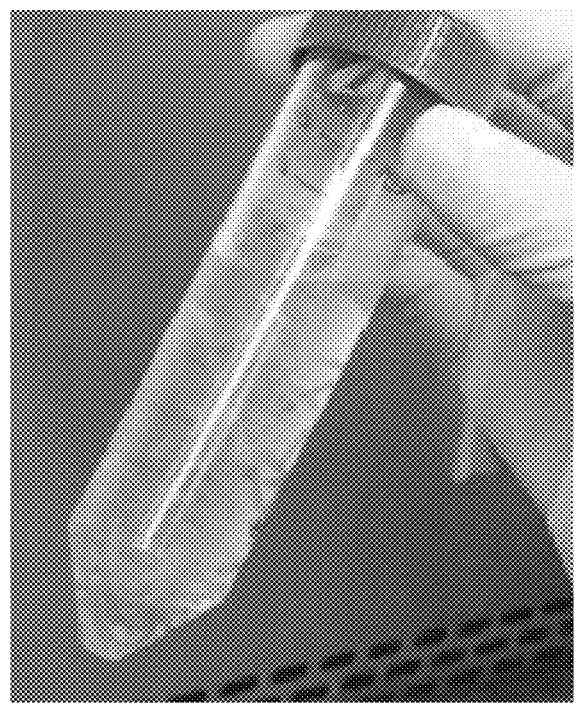
Figure 3E:

After co-cultivation, the explants were subjected to osmotic stress to reduce the concentration of *R. rhizogenes*. The explants were removed from the plate of ½ MS or ½ B5+3% sucrose media and placed in a volume of sterilized de-ionized water, as shown in FIG. 3D. The suspension of explants in the sterilized deionized water was agitated for about 30 minutes. The explants were then removed and transferred to a selection medium of ½ MS or ½ B5+3% sucrose+200 mg/L cefotaxime or 100 mg/L carbenicillin, as shown in FIG. 3E.

The plates of selection media containing the explants were then placed in an incubator at 25° C. and monitored for hairy root induction. Depending on the plant species, the explant source, and the *R. rhizogenes* strain used, hairy roots emerged within two to six weeks.

Figure 4A:
Figure 5A:
Figure 6A:
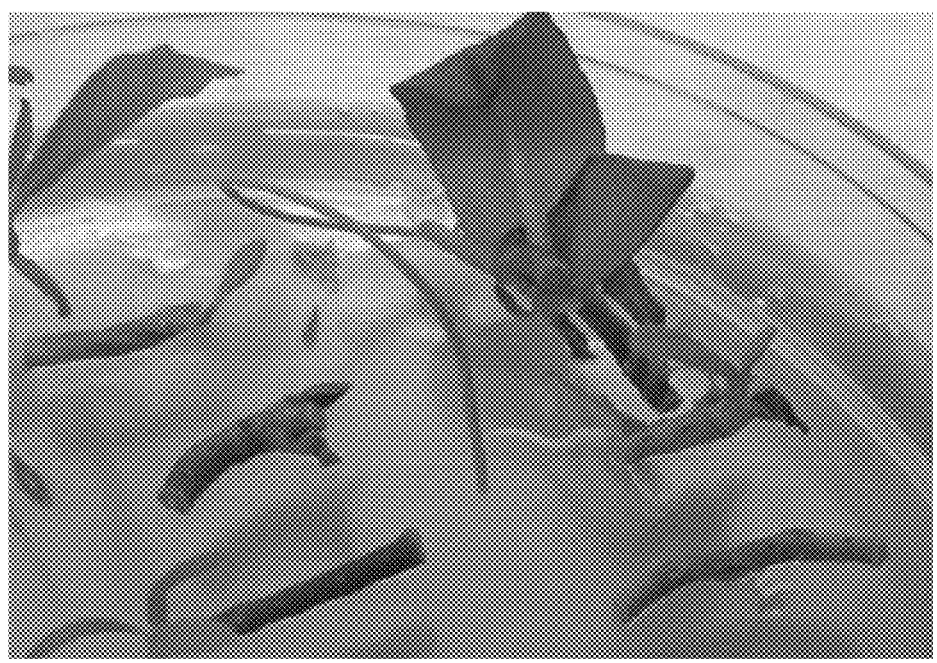

FIG. 4A illustrates in vitro induction of hairy roots on a tomato explant transformed with *Rhizobium rhizogenes* (strain ATCC 15834). FIG. 5A illustrates in vitro induction of hairy roots on a potato explant transformed with *Rhizobium rhizogenes*. FIG. 6 illustrates in vitro induction of hairy roots on citrus (Eureka lemon) explants transformed with *Rhizobium rhizogenes* (strain ATCC 15834).

The structures were confirmed as hairy roots using PCR amplification of known root inducing (Ri) DNA genes rolB and rolC.

Figure 4B:
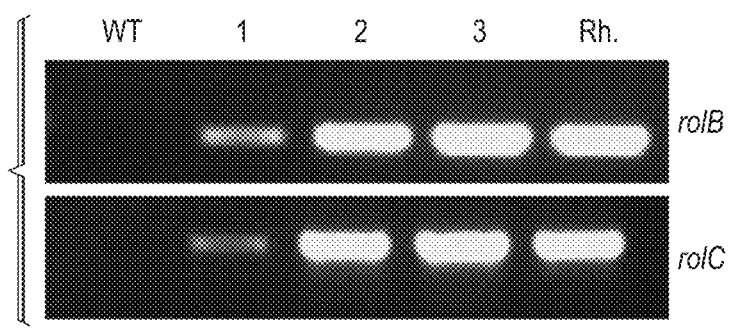

FIG. 4B shows PCR validation results of tomato hairy roots induced in vitro with *Rhizobium rhizogenes* (strain ATCC 15834), where rolB and rolC are marker genes for transformed hairy roots. As shown in FIG. 4B: lane WT shows PCR amplification of DNA from wild type tomato that was not transformed with *R. rhizogenes* (negative control); lane 1 shows PCR amplification of DNA from a hairy root of an explant transformed by *R. rhizogenes* strain Castlemart; lane 2 shows PCR amplification of DNA from a hairy root of an explant transformed by a *R. rhizogenes* strain from University of California 82 (UC82); lane 3 shows a PCR amplification of DNA from a hairy root of a second explant transformed by *R. rhizogenes* strain UC82; and lane Rh shows a PCR amplification of DNA from *R. rhizogenes* cells (positive control).

Figure 5B:
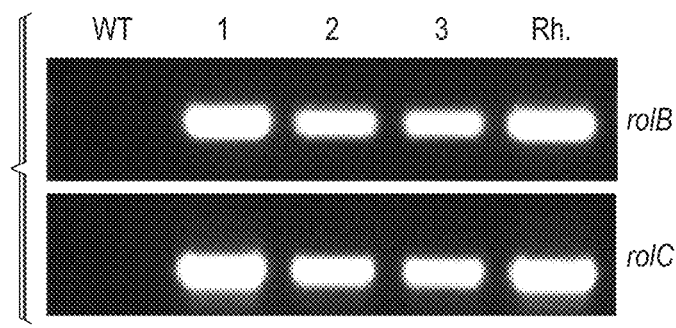

FIG. 5B shows PCR validation of potato (Atlantic) hairy roots from an explant transformed with *Rhizobium rhizogenes* (strain ATCC 15834), where rolB and rolC are marker genes for transformed hairy roots. Of the five lanes shown in FIG. 5B, Lane WT represents DNA from wild type potato (negative control), Lane 1 represents potato hairy root sample 1, Lane 2 represents potato hairy root sample 2, Lane 3 represents potato hairy root sample 3, and Lane Rh represents *R. rhizogenes* cells (positive control).

Figure 6B:

FIG. 6B shows PCR validation of citrus (Eureka lemon) hairy roots from an explant transformed with *Rhizobium*

*rhizogenes* (strain ATCC 15834). Of the two lanes for each of rolB and rolC shown in FIG. 6B, lanes marked HR (hairy roots) represent DNA from hairy roots, and Lane WT represents DNA from wild type citrus (negative control).

Example 4

In Planta Induction of Aerial Microbial Hairy Roots and Transgene Delivery

Healthy plants (control) and plants infected with Lso were selected, and select plant surfaces were surface sterilized using a solution containing 70% ethanol, 2.5% or 10% NaClO (bleach), and water. A suspension of *R. rhizogenes* was prepared as described in EXAMPLE 2.

Figure 7A:
Figure 7B:
Figure 8A:
FIG. 8B shows PCR validation results of aerial hairy roots on potato, according to an embodiment of the disclosure.
FIG. 8C shows PCR validation results of aerial microbial hairy roots on potato, according to an embodiment of the disclosure.

Induction of aerial microbial hairy roots was performed by gently wounding stem tissue and/or leaf tissue of a surface sterilized region of an Lso colonized plant using a needle dipped in the *R. rhizogenes* solution. The *R. rhizogenes* strain used contained both an Ri-DNA plasmid and a T-DNA plasmid with the T-DNA plasmid encoding a green fluorescent protein (GFP). Healthy plants were also induced for aerial hairy root formation using the method described above for use as an experimental control. The exposed wound sites were wrapped in aluminum foil to reduce exposure to light and help maintain desired humidity levels at the area of exposure. The plants were maintained in a growth chamber with appropriate temperature, light, and humidity conditions for each plant species. Plants were monitored for the formation of microbial hairy roots. FIG. 7A illustrates the formation of aerial hairy roots on a healthy tomato plant. FIG. 7B illustrates the formation of aerial microbial hairy roots on an Lso colonized tomato plant. FIG. 8A illustrates the formation of aerial microbial hairy roots on an Lso colonized potato plant.

Figure 7C:
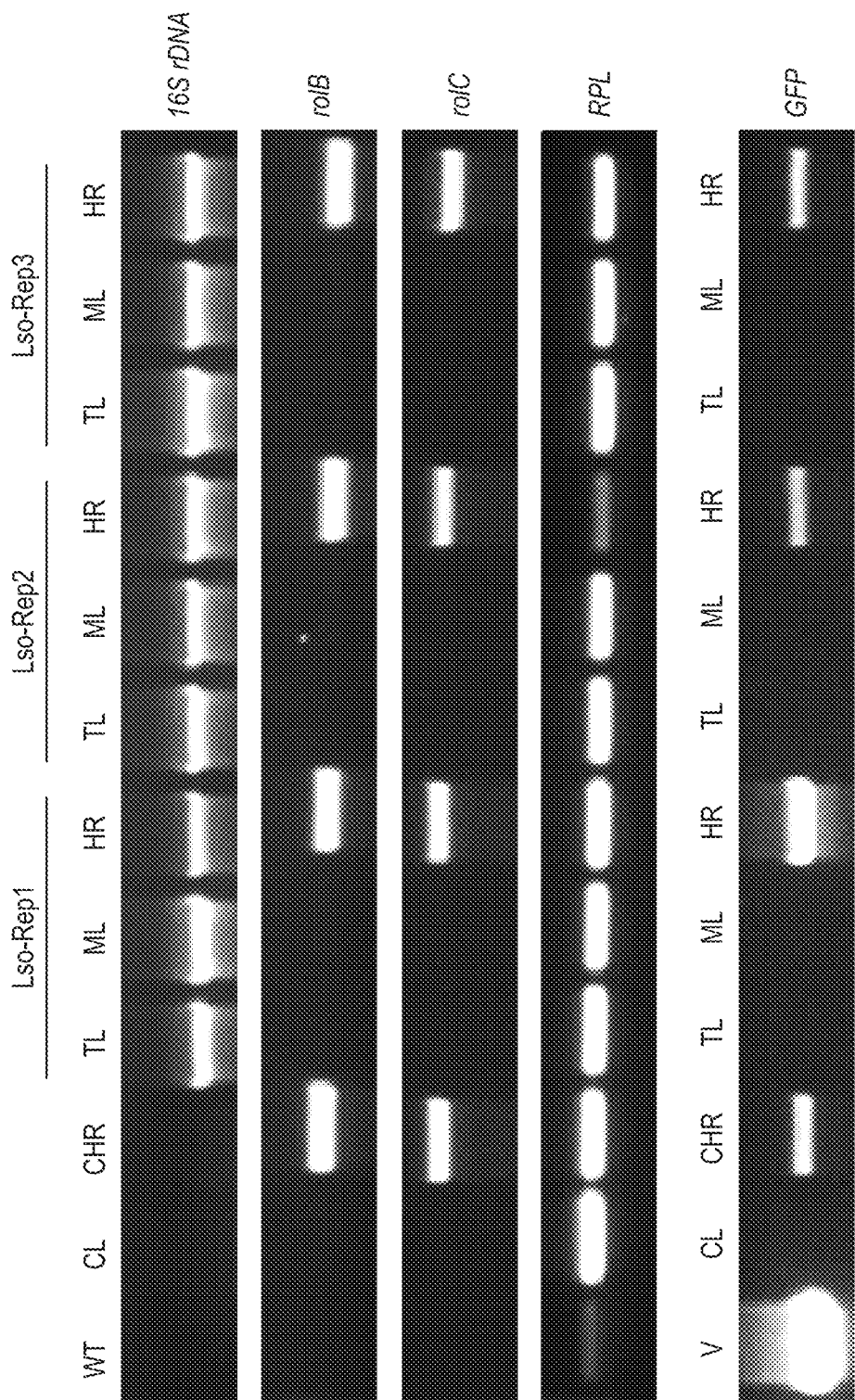

The structures were confirmed as microbial hairy roots using PCR amplification of known root inducing (Ri) DNA genes rolB and rolC. As shown in FIG. 7C, PCR validation of aerial microbial hairy root tissue was performed using DNA samples from microbial hairy roots pictured in FIGS. 7A and 7B. Primers were designed to amplify 16S rDNA of Lso (labelled in the row marked 16S rDNA), rolB and rolC marker genes from hair root transformation, an endogenous tomato gene RPL (control), and GFP gene encoded on the T-DNA plasmid. DNA from healthy plant tissue was gathered and amplified using the primer sets. The lanes of FIG. 7C representing healthy plant DNA are as follows: WT represents DNA from a wild type tomato plant (negative control), CL represents DNA from a healthy tomato leaf (negative control), and CHR represents DNA from a healthy hairy root (negative control for 16SrDNA primers). DNA was also extracted from Lso infected plant tissue including: a top leaf of an Lso infected tomato (TL), a middle leaf of an Lso infected tomato (ML), and an aerial microbial hairy root from an Lso infected tomato (HR). Three replicates were performed for the Lso infected tissue. As shown in FIG. 7C the CHR and HR samples replicated the rolB and rolC genes; thus showing that these were in fact hairy roots. The HR, but not CHR, amplified the 16S rDNA segments, establishing that the HR were Lso colonized.

A separate PCR gel was run to confirm the co-transformation of both the Ri-DNA plasmid (encoding rolB and rolC) and the T-DNA plasmid (encoding GFP). For this gel plasmid DNA comprising the T-DNA vector (labelled V) was extracted and amplified using the GFP primer set. As shown in FIG. 7C this served as a positive control for the amplification of GFP. FIG. 7C shows that in the CHR and HR samples the GFP gene was amplified, establishing that the Ri-DNA and T-DNA were co-transformed during the generation of the aerial hairy roots.

Figure 8B:
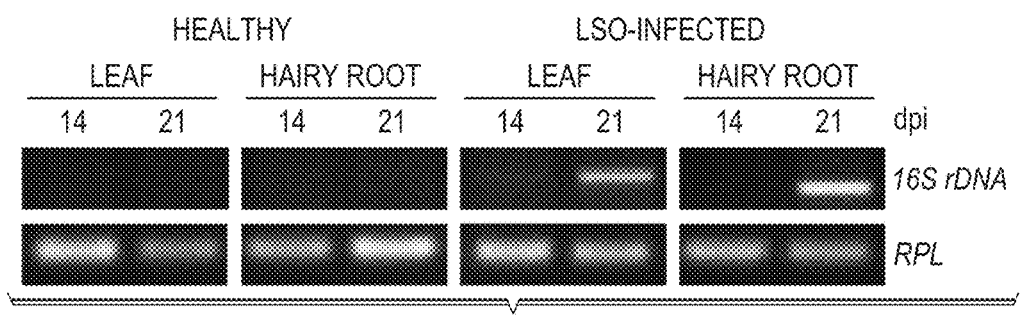
Figure 8C:
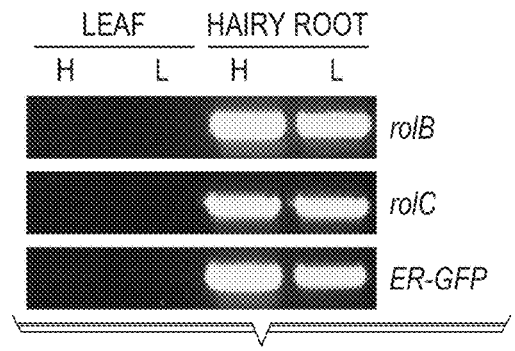

FIG. 8B illustrates the PCR amplification of 16S rDNA in 21 day old Lso-infected aerial hairy root samples taken from the Lso infected potato shown in FIG. 8A. Amplification of the RPL gene served as a positive control. FIG. 8C illustrates the PCR amplification of the rolB, rolC, and GFP genes in hairy root tissues from healthy ("H") potato plants and Lso infected ("L") potato plants; thus establishing that the Ri-DNA and T-DNA were co-transformed during the generation of the aerial hairy roots.

Example 5

In Planta Induction of Microbial Hairy Roots using a Rock Wool Method and Trans Gene Delivery Healthy tomato plants (control) and tomato plants infected with Lso were selected, and select plant surfaces were surface sterilized using a solution containing 70% ethanol, 2.5% or 10% NaClO (bleach), and water. A suspension of *R. rhizogenes* was prepared as described in Example 2. The *R. rhizogenes* contained both an Ri-DNA plasmid (including rolB and rolC genes) and a T-DNA plasmid encoding GFP.

A shoot portion of the selected tomato plants was removed using a scalpel and the wounded portion of the shoot was inserted in a rock wool matrix. A volume of the *R. rhizogenes* suspension was used to saturate the rock wool matrix, and the matrix was placed in a culture vessel to maintain a high humidity level. The *R. rhizogenes* was permitted to co-cultivate with the wound sites of the healthy tomato plants and the Lso infected tomato plants for 72 hours. After 72 hours the rock wool matrix was removed and the rock wool was permitted to dry, thereby killing most of the *R. rhizogenes*. The rock wool matrix was exposed to the ambient environment for approximately 24 hours before being rehydrated. The treated shoot and rock wool matrix was transferred to a new plastic magenta box culture vessel with nutrient solution (½ MS or ½ B5), and placed in a diurnal growth chamber and monitored for generation of microbial hairy roots.

Figure 9A:
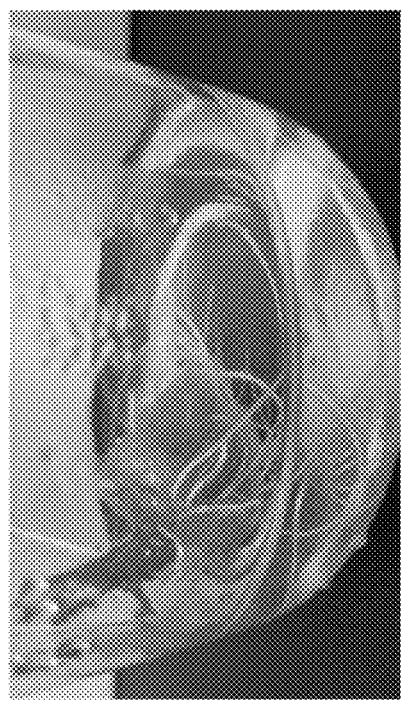
FIG. 9A shows microbial hairy roots induced on an Lso-colonized tomato using a rock wool method, according to an embodiment of the disclosure.
Figure 9A:
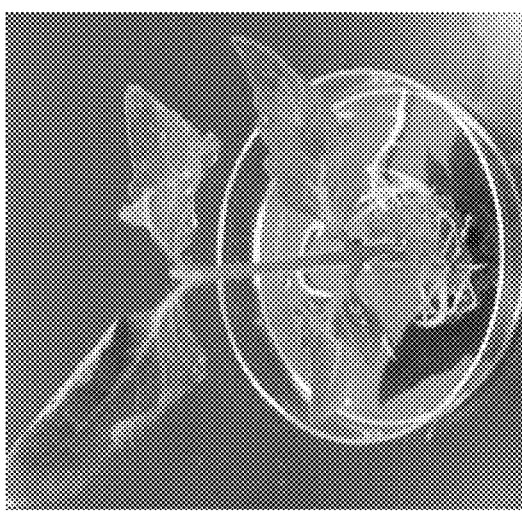

FIG. 9A shows the generation of microbial hairy roots on an Lso infected tomato plant.

Figure 9B:
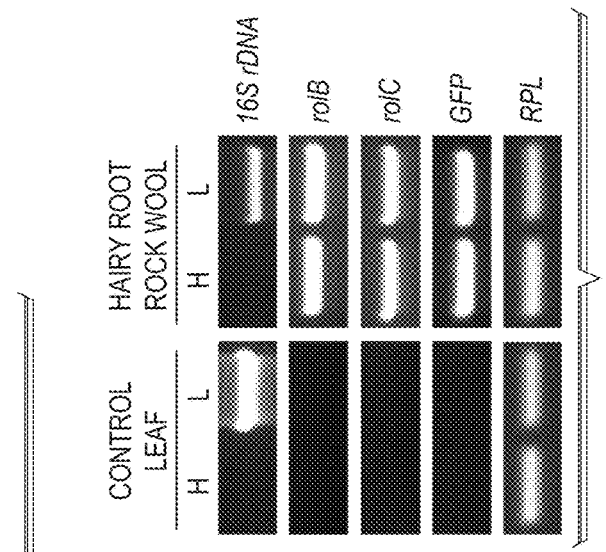
FIG. 9B shows PCR validation results of microbial hairy roots on tomato induced using a rock wool method, according to an embodiment of the disclosure.

PCR validation was performed to confirm the microbial hairy root constructs, the colonization of the microbial roots with Lso, and the co-transformation with both the Ri-DNA and T-DNA plasmids. FIG. 9B illustrates the PCR amplification of rolB, rolC, and GFP genes in hairy root tissues from healthy ("H") potato plants and Lso infected ("L") potato plants; thus establishing that the Ri-DNA and T-DNA were co-transformed during the co-cultivation with *R. rhizogenes*. As expected, the 16SrDNA was only amplified in the Lso infected microbial hairy roots.

Example 6

In Planta Induction of Microbial Hairy Roots using a Vermiculite Method and Trans Gene Delivery Healthy plants (control) and plants infected with Lso were selected, and select plant surfaces were surface sterilized using a solution containing 70% ethanol, 2.5% or 10% NaClO (bleach), and water. A suspension of *R. rhizogenes* was prepared as described in EXAMPLE 2. The *R. rhizo-* genes contained both an Ri-DNA plasmid (including rolB and rolC genes) and a T-DNA plasmid encoding GFP.

A shoot portion of the selected plants was removed using a scalpel and the wounded portion of the shoot was submerged in the *R. rhizogenes* suspension. A vacuum environment of about 30 inHg was generated and held for 30 minutes. After release of the vacuum, the shoot was removed from the *R. rhizogenes* suspension and placed in a vermiculite matrix. The shoots were placed in a covered tray in a growth chamber at 25° C. with a light/dark cycle of 14 hours of light followed by 10 hours of dark. The shoots were monitored for microbial hairy root generation.

Figure 10A:
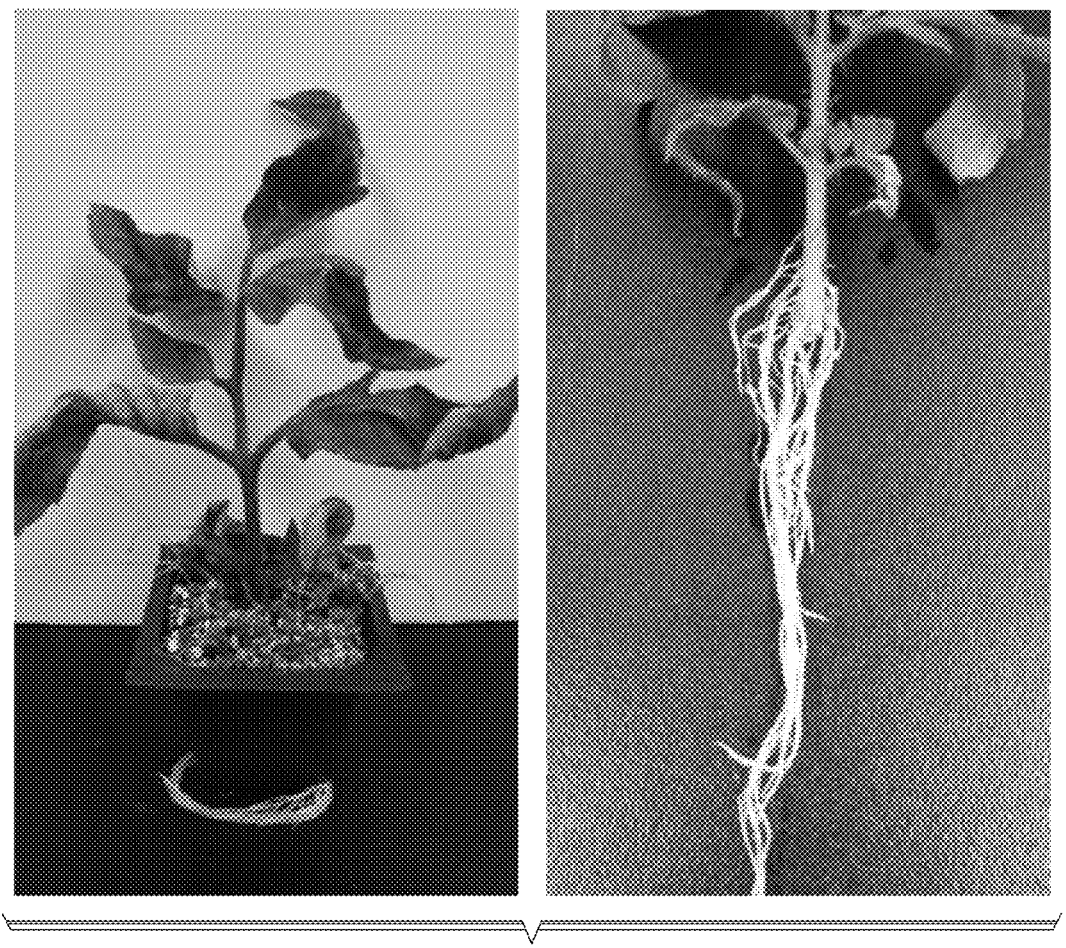
FIG. 10A shows microbial hairy roots induced on a tomato plant using a vermiculite method, according to an embodiment of the disclosure.
Figure 10B:
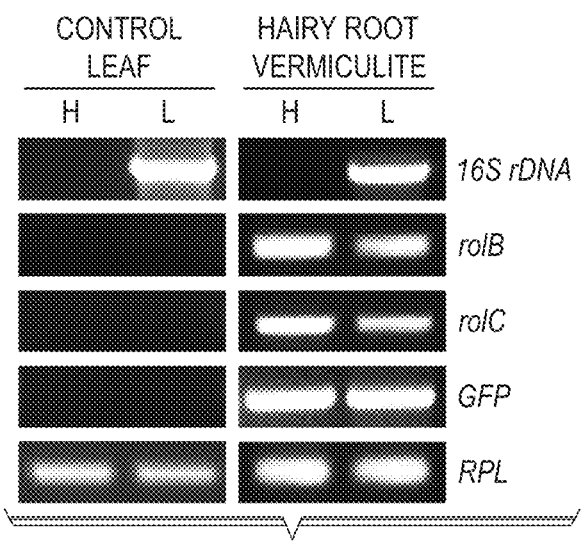
FIG. 10B shows PCR validation results of microbial hairy roots on tomato induced using a vermiculite method, according to an embodiment of the disclosure.

FIG. 10A illustrated microbial hairy root growth from a tomato plant induced using the vermiculite method. PCR validation was performed to confirm the microbial hairy root constructs, the colonization of the microbial roots with Lso, and the co-transformation with both the Ri-DNA and T-DNA plasmids. FIG. 10B illustrates the PCR amplification of rolB, rolC, and GFP genes in hairy root tissues from healthy ("H") tomato plants and Lso infected ("L") tomato plants; thus establishing that the Ri-DNA and T-DNA were co-transformed during the co-cultivation with *R. rhizogenes*. As expected, the 16S rDNA was only amplified in the Lso infected microbial hairy roots.

Figure 11:
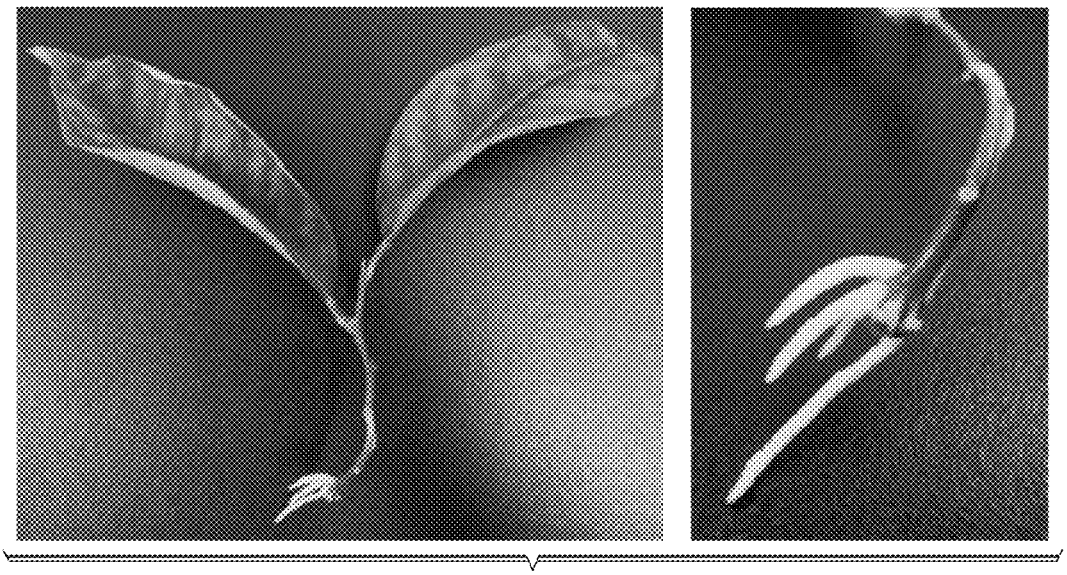
FIG. 11 shows microbial hairy roots induced on a Las infected citrus (sour orange) using a vermiculite method, according to an embodiment of the disclosure.

FIG. 11 illustrates the generation of microbial hairy roots from shoots of citrus (Sour orange) using the vermiculite method.

Example 7

Propagation of Hairy Roots—Vermiculite Method

A harvested hairy root may be clonally propagated. Clonal propagation of a harvested hairy root may provide an increased source of a fastidious microbe contained within a harvested hairy root (e.g., a microbial hairy root inoculum).

Hairy roots generated from both healthy tomato plants and Lso infected tomato plants, as described above in EXAMPLE 4, were selected for propagation. The tomato plants were cut directly below the site where aerial hairy roots generated and the lower stem and root portion of the plant was discarded. The shoot portion attached to the aerial hairy roots was maintained (i.e., an attached hairy root).

Figure 12:
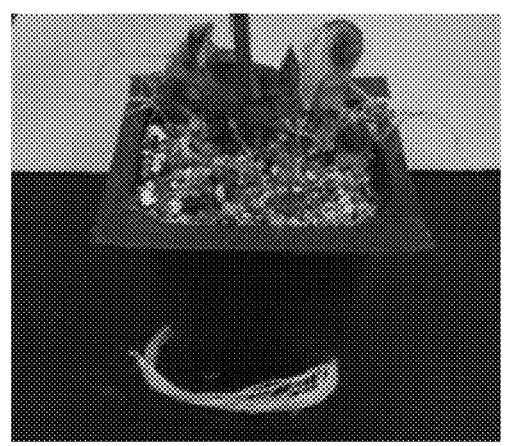
FIG. 12 illustrates propagated hairy roots growing in a vermiculite matrix, according to an embodiment of the disclosure.

The aerial hairy roots were surface sterilized by submerging the roots in a 70% ethanol solution, 2.5% or 10% bleach solution, and then rinsing with de-ionized water. The attached hairy roots were then transplanted into a vermiculite matrix. The transplanted attached hairy roots were placed in a growth chamber at 25° C. with a light/dark cycle of 14 hours of light followed by 10 hours of dark. The shoots were monitored for propagation of the hairy roots. FIG. 12 illustrates the propagated hairy roots growing from the bottom of a vermiculite containing pot.

Example 8

Propagation of Microbial Hairy Roots—Hydroponic Method

Figure 13:
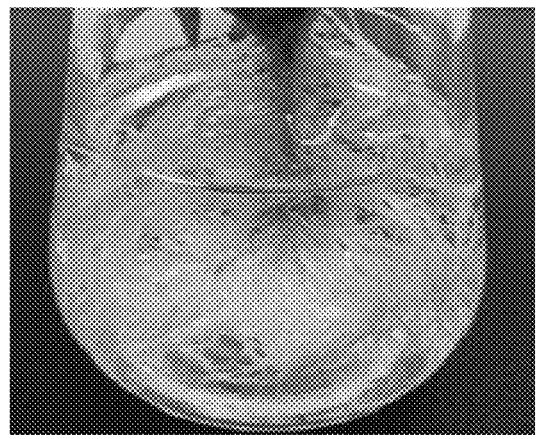
FIG. 13 illustrates propagated hairy roots growing in a hydroponic culture, according to an embodiment of the disclosure.

Hairy roots generated from both healthy tomato plants and Lso infected tomato plants, as described above in EXAMPLE 4, were selected for propagation. The aerial hairy roots of the tomato plants were harvested when they reached a length of at least 3 cm. The harvested aerial hairy roots were surface sterilized by submerging the harvested roots in a 70% ethanol solution, 2.5% or 10% bleach solution, and then rinsing with de-ionized water. The harvested hairy roots were then placed in a beaker containing ½ MS or ½ B5+3% sucrose+200 mg/L cefotaxime or 100 mg/L carbenicillin, and 2.5 mg/L amphotericin B. The hydroponic culture was maintained at 25° C. with gentle agitation at 50 or 100 rpm. FIG. 13 illustrates the propagated hairy roots growing in a hydroponic culture.

Example 9

Propagation of Microbial Hairy Roots—In vitro Method

Figure 14:
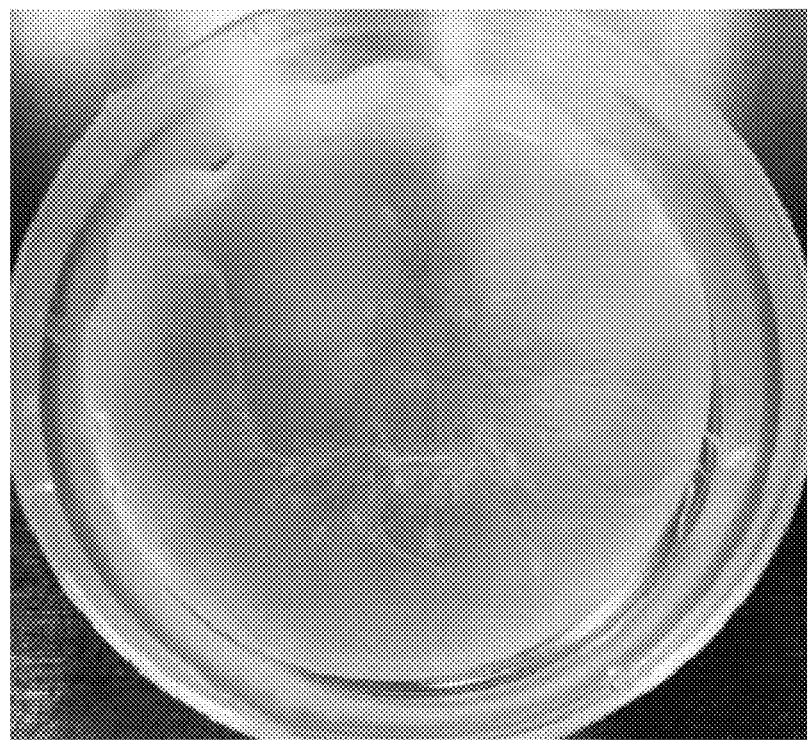
FIG. 14 illustrates propagated hairy roots growing in an in vitro culture, according to an embodiment of the disclosure.

Hairy roots generated from both healthy tomato plants and Lso infected tomato plants, as described above in EXAMPLE 4, were selected for propagation. The aerial hairy roots of the tomato plants were harvested when they reached a length of at least 3 cm. The harvested aerial hairy roots were surface sterilized by submerging the harvested roots in a 70% ethanol solution, 2.5% or 10% bleach solution, and then rinsing with de-ionized water. The harvested hairy roots were then placed on a plate containing ½ MS or ½ B5+3% sucrose+200 mg/L cefotaxime or 100 mg/L carbenicillin, and 2.5 mg/L amphotericin B. The in vitro culture was maintained at 25° C. FIG. 14 illustrates the propagated hairy roots growing in a hydroponic culture. The nutrient media was replaced with fresh media on a weekly basis.

Example 10

Propagation of Microbial Hairy Roots—Bioreactor Method

Figure 15:
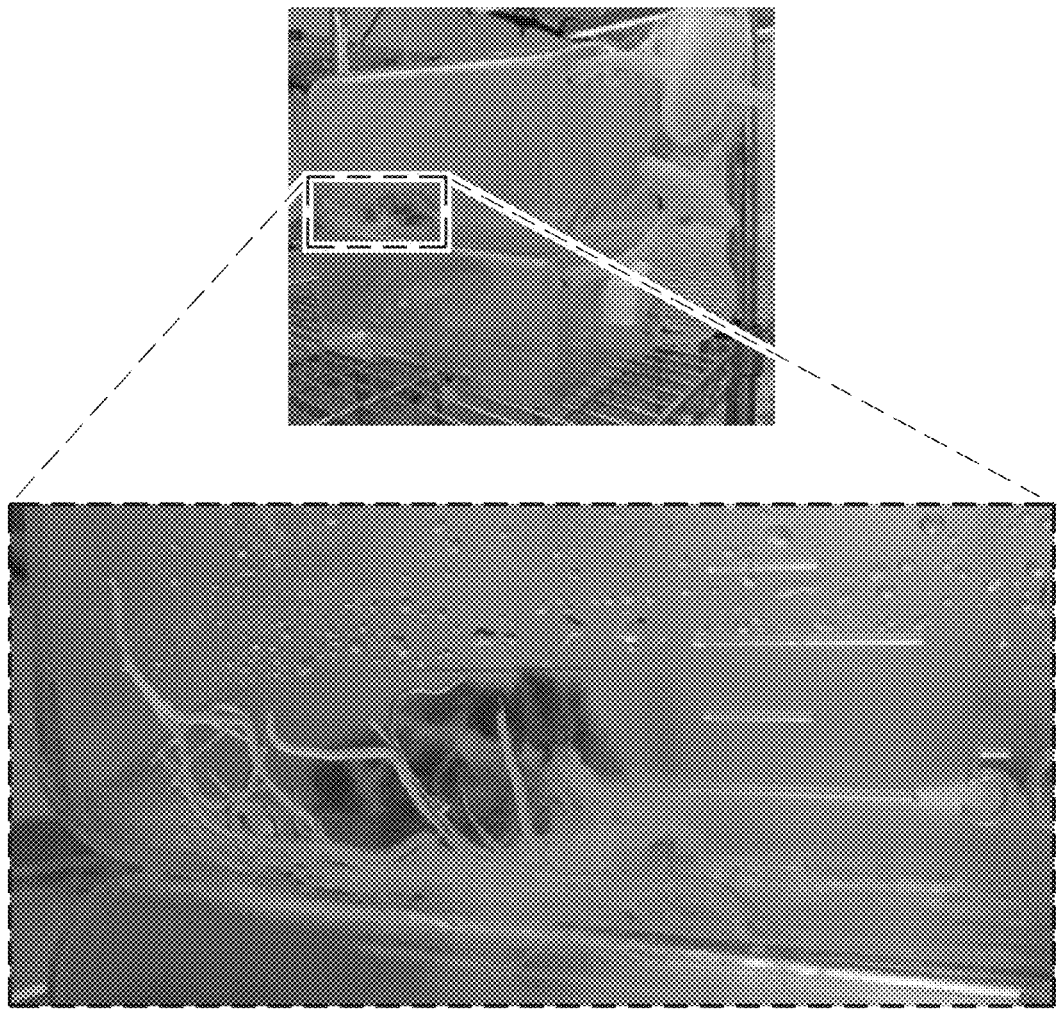
FIG. 15 illustrates propagated hairy roots growing in a bioreactor system, according to an embodiment of the disclosure.

Hairy roots generated from both healthy tomato plants and Lso infected tomato plants, as described above in EXAMPLE 9, were selected for propagation using a bioreactor method. The hairy roots were harvested from the in vitro culture or in planta methods, were surface sterilized by submerging the harvested roots 70% ethanol solution, 2.5% or 10% bleach solution, and then rinsing with de-ionized water. and placed in a SETIS system containing ½ MS or ½ B5+3% sucrose+200 mg/L cefotaxime or 100 mg/L carbenicillin, and 2.5 mg/L amphotericin B. The bioreactor culture was maintained at 25° C. FIG. 15 illustrates the propagated hairy roots growing in a bioreactor system. The nutrient media was replaced with fresh media every three to four weeks.

Example 11

High-Throughput Antimicrobial Assays

Figure 16A:
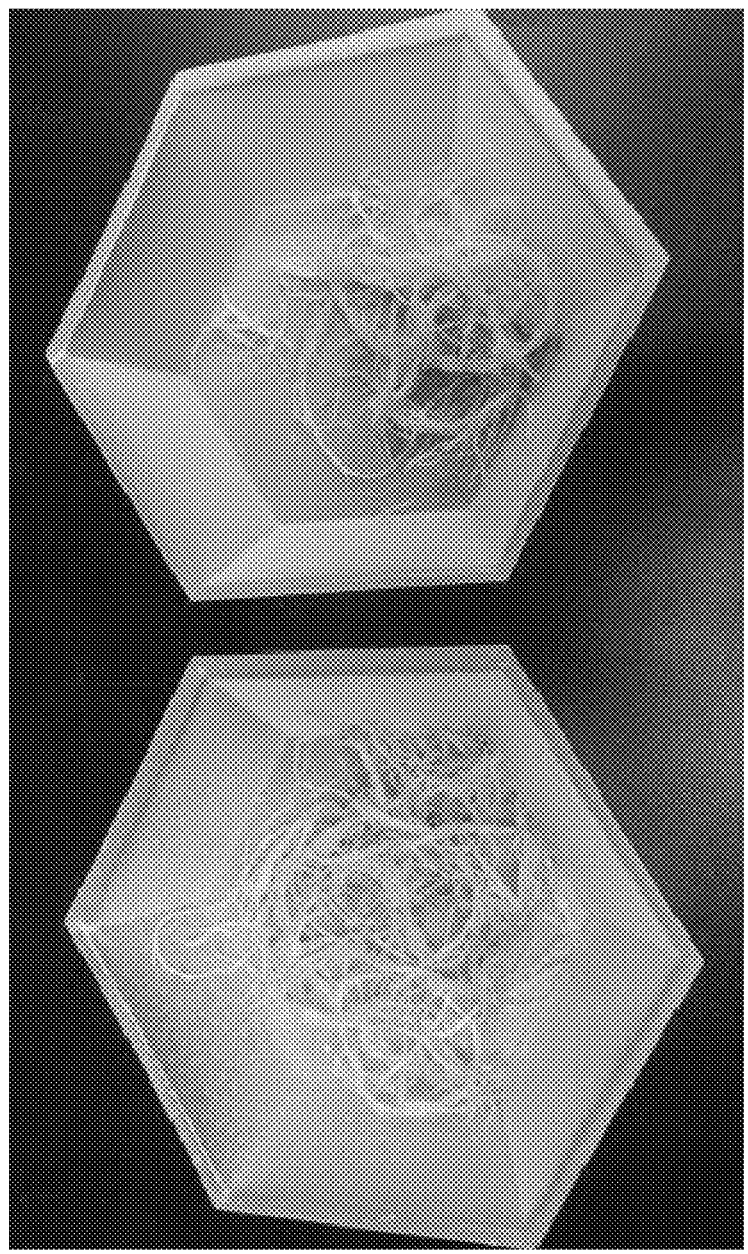
FIG. 16A shows healthy and Lso-colonized hairy roots harvested from an in vitro or in planta system, according to an embodiment of the disclosure.
Figure 16B:
FIG. 16B shows healthy and Lso-colonized microbial hairy roots distributed into a multi-well plate, according to an embodiment of the disclosure.

Microbial hairy roots were used to analyze whether Lso is inhibited by antimicrobials such as penicillin. As shown in FIG. 16A, healthy hairy roots and Lso colonized microbial hairy roots were harvested from either in vitro or in planta propagation. The hairy roots were separated and weighed into equal quantities (e.g., 50 or 100 mg/per well) without damaging the structural integrity. Healthy hairy roots and Lso colonized microbial hairy roots were similarly distributed into three or more biological replicates into wells of a multi-well plate, as shown in FIG. 16B. Two milliliters of ½ MS or ½ B5 media was placed into each of the control wells of the multi-well plate, submerging the hairy roots, serving as the negative control. Two milliliters of ½ MS or ½ B5+100 mg/L penicillin media was placed into each of the experimental wells of the multi-well plate, submerging the hairy roots. The multi-well plate was placed in a vacuum environment and a pressure of 25 inHg was drawn for a period of 15 to 30 minutes. The multi-welled plates with hairy roots were covered with aluminum foil to prevent light exposure and possible degradation of antibiotics. The multi-welled plates with their respective treatments were then incubated at a temperature of 25° C. with gentle shaking on a shaker (50 rpm) for a period of 2 days and 7 days.

Figure 16C:
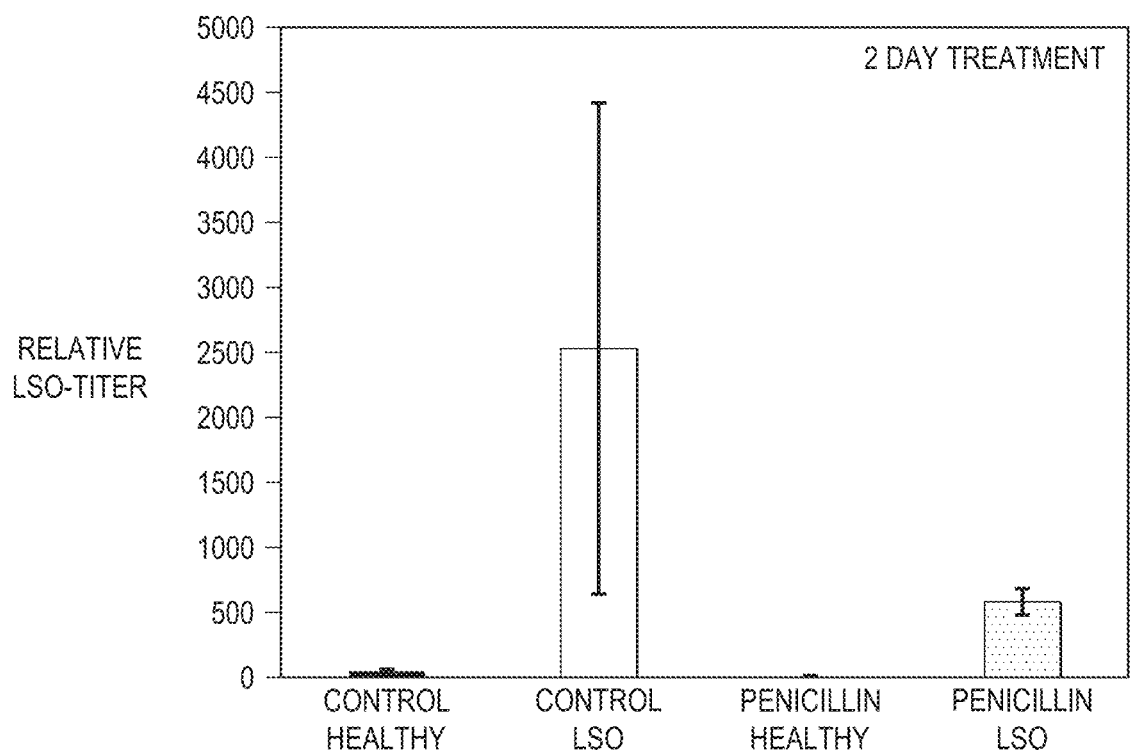
FIG. 16C shows Quantitative Real Time PCR results of an Lso titer after a 2 day treatment of hairy roots with penicillin.
Figure 16D:
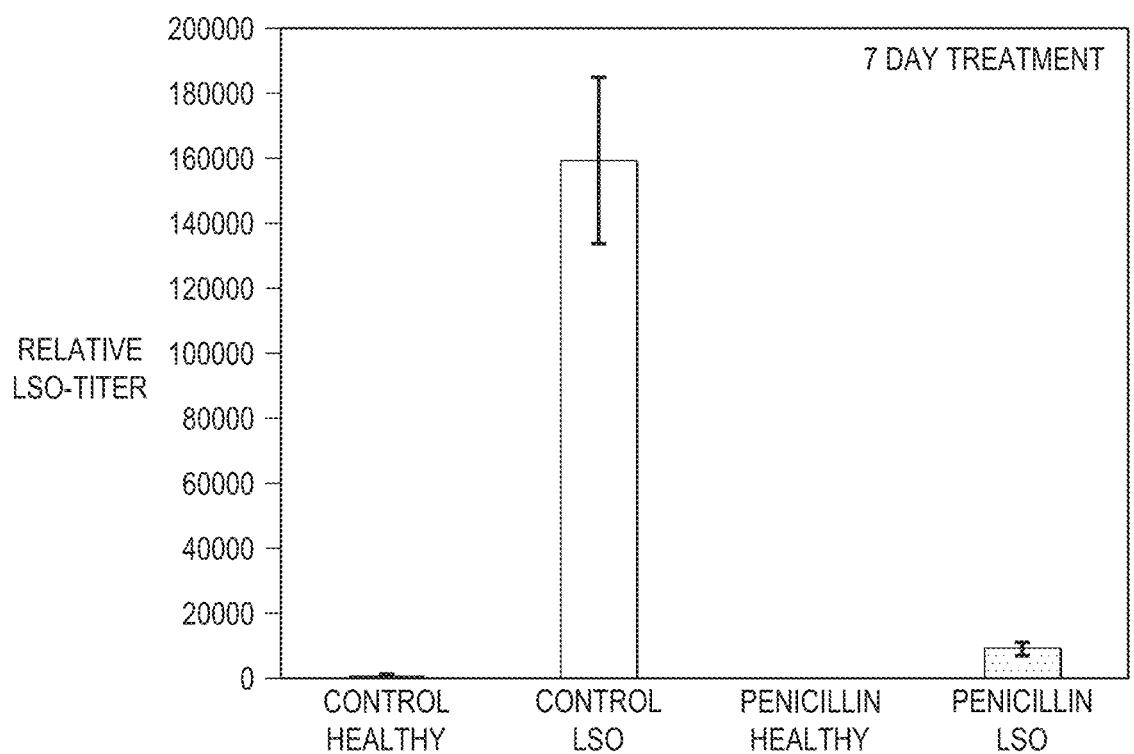
FIG. 16D shows Quantitative Real Time PCR results of an Lso titer after a 7 day treatment of hairy roots with penicillin.

Quantitative Real Time PCR was used to evaluate the Lso titer using primers to amplify 16s rDNA sequences. As shown in FIGS. 16C and 16D, the Lso colonized microbial hairy roots exposed to penicillin showed a significantly lower titer of Lso than the Lso colonized microbial hairy roots that were not exposed to penicillin after both 2 days and 7 days of exposure.

What is claimed is:

1. A method for cultivating a plant microbe, wherein the plant microbe is a vascular-colonizing microbe selected from the group consisting of *Xylella fastidiosa* spp. and *Candidatus Liberibacter* spp., the method comprising:
- contacting a plant with the plant microbe;
- selecting tissues from one or more parts of the plant colonized with the plant microbe as an explant source to create an explant;
- manually contacting the explant colonized by the plant microbe with a suspension of *Rhizobium rhizogenes* under conditions that permit induction of hairy roots to form a colonized hairy root; and
- propagating the colonized hairy root to form a propagated hairy root.

2. The method according to claim 1, wherein the plant is selected from a tomato plant, a potato plant, and a citrus plant.

3. The method according to claim 1, wherein the *Candidatus Liberibacter* spp. is selected from the group consisting of *Candidatus Liberibacter* solanacearum (Lso) and *Candidatus Liberibacter* asiaticus (Las).

4. The method according to claim 1, wherein contacting the explant colonized by the plant microbe with the suspension of *Rhizobium rhizogenes* further comprises wounding one or more surfaces of the explant to form a wound site, and exposing the wound site to the suspension of *Rhizobium rhizogenes*.

5. The method according to claim 1, wherein contacting the explant colonized by the plant microbe with the suspension of *Rhizobium rhizogenes* further comprises:
- removing a photosynthetic portion of the explant to generate a wound site;
- covering the wound site with a rock wool matrix; and
- exposing the rock wool matrix to the suspension of *Rhizobium rhizogenes*.

6. The method according to claim 1, wherein contacting the explant colonized by the plant microbe with the suspension of *Rhizobium rhizogenes* further comprises:
- removing a photosynthetic portion of the explant to generate a wound site;
- submerging the wound site in the suspension of *Rhizobium rhizogenes;*
- vacuum infiltrating at least a portion of the suspension of *Rhizobium rhizogenes* into the wound site; and
- covering the wound site with a vermiculite matrix.

7. The method according to claim 1 further comprising assessing the presence of the plant microbe in the propagated hairy root using polymerase chain reaction (PCR) amplification of a marker gene.

8. The method according to claim 1, wherein propagating the colonized hairy root to form a propagated hairy root further comprises:
- exposing an attached hairy root or a harvested hairy root to one or more selective conditions;
- transferring the attached hairy root or the harvested hairy root to at least one of:
- a vermiculite matrix,
- a hydroponic system,
- an in vitro system, and
- a bioreactor system.

9. The method according to claim 1, wherein *Rhizobiurn rhizogenes* comprises both a Ri-DNA plasmid and a T-DNA plasmid, and wherein the T-DNA plasmid comprises a first exogenous transgene.

10. The method according to claim 9, wherein the first exogenous transgene encodes an auto-fluorescent protein.

11. The method according to claim 1, wherein the explant comprises a first exogenous transgene.

12. A method for assessing an effect of a test composition on a plant, microbe wherein the plant microbe is is a vascular-colonizing microbe selected from the group consisting of *Xylella fastidiosa* spp. and *Candidatus Liberibacter* spp., the method comprising:
- contacting a plant colonized by the plant microbe with a suspension of *Rhizobium rhizogenes* under conditions that permit induction of hairy roots colonized by the plant microbe to form a colonized hairy root;
- propagating the colonized hairy root to form a propagated hairy root;
- manually contacting the propagated hairy roots with the test composition;
- and assessing at least one metric of the presence or vitality of the plant microbe.

13. The method according to claim 12, wherein the plant is selected from a tomato plant, a potato plant, and a citrus plant.

14. The method according to claim 12, wherein the *Candidatus Liberibacter* spp. is selected from the group consisting of *Candidatus Liberibacter* solanacearum (Lso) and *Candidatus Liberibacter* asiaticus (Las).

15. The method according to claim 12, wherein the test composition is conditionally or constitutively present in the infected plant.

16. The method according to claim 15, wherein the plant colonized by the plant microbe comprises at least one of an exogenous transgene, a CRISPR/Cas, a TALEN, and an RNAi construct, and wherein the test composition is or comprises, respectively, a gene product of the transgene, the CRISPR/Cas, the TALEN, and the RNAi construct.

17. The method according to claim 9, wherein the exogenous transgene encodes a NPR1 protein.

18. A method of culturing a plant microbe using hairy roots, wherein the plant microbe is a vascular-colonizing microbe selected from the group consisting of *Xylella fastidiosa* spp. and *Candidatus Liberibacter* spp., the method comprising:
- selecting tissues from one or more parts of a plant colonized by at least one microbe as an explant source;
- cultivating the explant source in a medium comprising *Rhizobium rhizogenes;*
- cutting the explant source into a plurality of pieces;
- inducing growth of hairy roots from at least some pieces of the explant source;
- confirming hairy root growth; and
- confirming a presence of the plant microbe in the hairy roots.

19. The method of culturing plant microbes according to claim 18, wherein the plant comprises a first exogenous transgene and a second exogenous transgene.

20. The method of culturing plant microbes according to claim 19, wherein the first exogenous transgene encodes an auto-fluorescent protein.

21. The method of culturing plant microbes according to claim 19, wherein the medium is free of cefatoxime, carbencillin and kanamycin.

22. The method of culturing plant microbes according to claim 18,
- wherein confirming hairy root growth comprises performing polymerase chain reaction amplification of *Rhizobium rhizogenes* rolB or rolC marker genes, or
- wherein confirming the presence of the plant microbe in the hairy roots comprises performing PCR amplification of a 16S rDNA marker gene of the plant microbe.

23. A method for cultivating a plant microbe, wherein the plant microbe is a vascular-colonizing microbe selected from the group consisting of *Xylella fastidiosa* spp. and *Candidatus Liberibacter* spp., the method comprising:
- selecting a tissue from one or more parts of a plant as an explant source to make an explant;
- manually contacting the explant with a suspension of *Rhizobium rhizogenes* under conditions that permit induction of hairy roots to form a hairy root on the explant; propagating the hairy root to form a propagated hairy root; and
- manually contacting the propagated hairy root with the plant microbe to form a plant colonized hairy root.

\* \* \* \* \*